US005846189A

United States Patent [19]
Pincus

[11] Patent Number: 5,846,189
[45] Date of Patent: Dec. 8, 1998

[54] SYSTEM FOR QUANTIFYING ASYNCHRONY BETWEEN SIGNALS

[76] Inventor: Steven M. Pincus, 990 Moose Hill Rd., Guilford, Conn. 06437

[21] Appl. No.: 757,258

[22] Filed: Nov. 27, 1996

Related U.S. Application Data

[63] Continuation-in-part of Ser. No. 716,059, Sep. 19, 1996, Pat. No. 5,769,793, which is a continuation-in-part of Ser. No. 011,409, Jan. 29, 1993, Pat. No. 5,562,596, which is a continuation-in-part of Ser. No. 404,737, Sep. 8, 1989, Pat. No. 5,191,524.

[51] Int. Cl.⁶ ..................................................... A61B 5/00
[52] U.S. Cl. ........................ 600/301; 600/484; 600/544; 600/515; 128/897; 128/898; 128/920; 128/923; 364/130; 705/10
[58] Field of Search ................................... 600/300, 301, 600/481, 483, 484, 509, 515, 518, 544, 551; 128/920, 923, 897, 898; 364/130; 705/10, 35, 36

[56] References Cited

U.S. PATENT DOCUMENTS

| | | | |
|---|---|---|---|
| 4,018,219 | 4/1977 | Hojaiban | 128/2.06 A |
| 4,680,708 | 7/1987 | Ambos et al. | 364/417 |
| 4,732,157 | 3/1988 | Kaplan et al. | 128/696 |
| 4,802,491 | 2/1989 | Cohen et al. | 128/702 |
| 4,932,610 | 6/1990 | Maestrello | 244/203 |
| 4,934,374 | 6/1990 | Ostlund et al. | 128/695 |
| 4,974,162 | 11/1990 | Siegel et al. | 364/413.06 |
| 5,112,292 | 5/1992 | Hwang et al. | 600/16 |
| 5,222,698 | 6/1993 | Nelson et al. | 244/203 |

OTHER PUBLICATIONS

Pincus, S.M., et al., "A Regularity Statistic for Medical Data Analysis," *J. Clin. Monit.*, 7(4) :335–345, (Oct. 1991).
Kaplan, D.T., et al., "Aging and the Complexity of Cardiovascular Dynamics," *Biophys. J.*, 59:945–949, (Apr. 1991).
Lipsitz, L.A., et al., "Loss of 'Complexity' and Aging," *JAMA*,267 (13) :1806–1809, (Apr. 1992).
Pincus, S.M., et al., "Quantification of Hormone Pulsatility Via An Approximate Entropy Algorithm," *Am. J. Physiol.* 262 (Endocrinol. Metab. 25), pp. E741–E754, (1992).
Pincus, S.M., et al., "Approximate Entropy: A Regularity Measure for Fetal Heart Rate Analysis," *Obstet. Gynecol.*, 79 (2) :249–255, (Feb. 1992).
Fox, R.W., et al., "Introduction to Fluid Mechanics," 2d Ed., John Wiley & Sons: New York 1978, pp. 38–46, 316, 332–333, 354–367, 424–462.
Pincus, S., et al., "Randomness and degrees of irregularity," *Proc. Natl. Acad. Sci.*, 93:2083–2088, (Mar. 1996).
Gleick, J., "CHAOS: Making a New Science," Viking Penguin Inc., New York, NY, pp. 275–300, (1987).
Eckmann, J.P., et al., "Ergodic Theory of Chaos and Strange Attractors," *Reviews of Modern Physics*, 57(3), (Jul. 1985).
Browne, M.W., "In Heartbeat, Predictability Is Worse Than Chaos," *The New York Times*, (Jan. 1989).
Billingsley, P., "Ergodic Theory and Information," New York: Wiley, 1965: pp. 60–94.
Grassberger, P., et al., "Estimation of the Kolmogorov Entropy from a Chaotic Signal," *Physical Review A*, 28(4):2591–2593, (Oct. 1983).

(List continued on next page.)

*Primary Examiner*—William E. Kamm
*Assistant Examiner*—Kennedy J. Schaetzle
*Attorney, Agent, or Firm*—Hamilton, Brook, Smith & Reynolds, P.C.

[57] ABSTRACT

A data processing environment processes a plurality of signals to detect a system state. The specific system can be, for example, a living human, where the signals are biological parameters. A processor operates the data points from two signals by defining respective classes of contiguous runs of a prescribed length of the data. The processor then assigns quantitative values to measure the regularity and stability of similar patterns between the first and second sets of classes of data points from the defined classes. These assigned quantitative values are aggregated to quantify the degree of asynchrony or conditional irregularity between the signals.

38 Claims, 18 Drawing Sheets

OTHER PUBLICATIONS

Zbilut, J.P., et al., "Decreased Heart Rate Variability in Significant Cardiac Events," *Crit. Care Med.*, 16(1) :64–66, Abstract Only, (1988).

Inouye, T., et al., "Quantification of EEG Irregularity by use of the Entropy of the Power Spectrum," 79(3) :204–210, *Electroencephalogr. Clin. Neurophysiol*, Abstract Only, (1991).

Pincus, S.M., et al., "Approximate Entropy: Statistical Properties and Applications," *Commun. Statist. —Theory Meth.*, 21 (11) :3061–3077, (1992).

Pincus, S.M., "Approximating Markov Chains," *Proc. Natl. Acad. Sci. USA*, 89:4432–4436, (May 1992).

Pincus, S.M., "Approximate Entropy as a Measure of System Complexity," *Proc. Natl. Acad., Sci. USA*, 88:2297–2301, (Mar. 1991).

Parer, W.J., et al., "Validity of Mathematical Methods of Quantitating Fetal Heart Rate Variability," *Am. J. Obstet. Gynecol.*, 153(4) :402–409, (Oct. 1995).

| SLOT  | U(1) | U(2) | U(3) | U(4) | U(5) | U(6) | U(7) | U(8) | U(9) |
|-------|------|------|------|------|------|------|------|------|------|
| VALUE | 1    | 0    | 1    | 0    | 1    | 0    | 1    | 0    | 1    |
FIG. 2A
| SLOT  | U(1) | U(2) | U(3) | U(4) | U(5) | U(6) | U(7) | U(8) | U(9) |
|-------|------|------|------|------|------|------|------|------|------|
| VALUE | *    | *    | 1    | *    | *    | 0    | *    | *    | 1    |
* Random where both zero and one occur with probability $\frac{1}{2}$
FIG. 2B
FIG. 4A
FIG. 4B
FIG. 4C

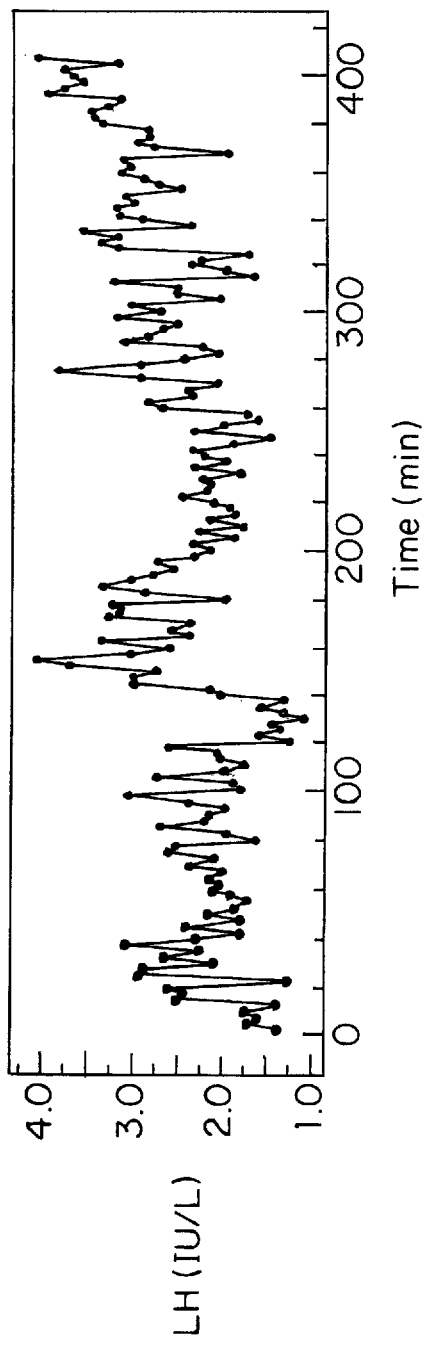
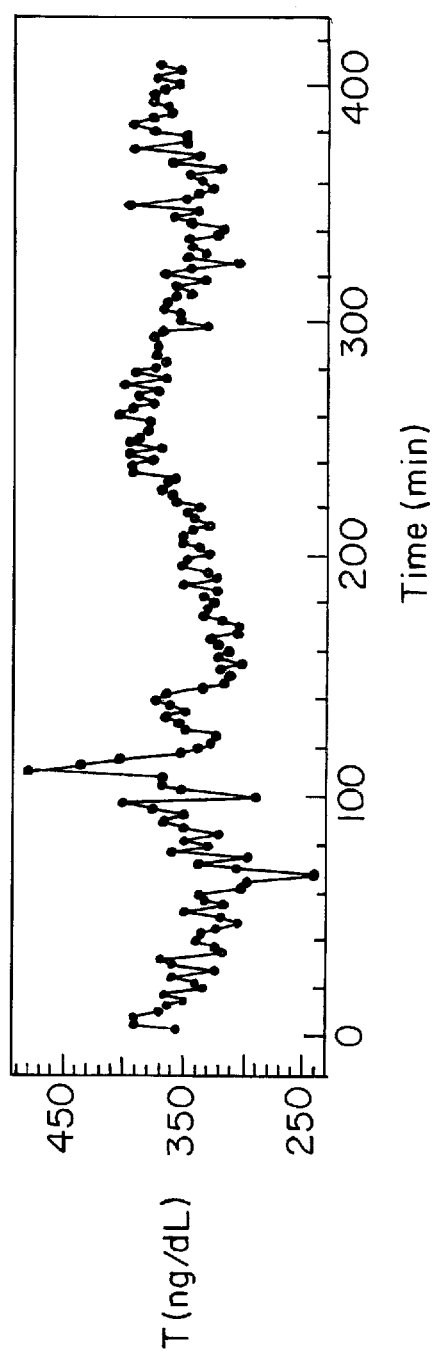
FIG. 15A
FIG. 15B

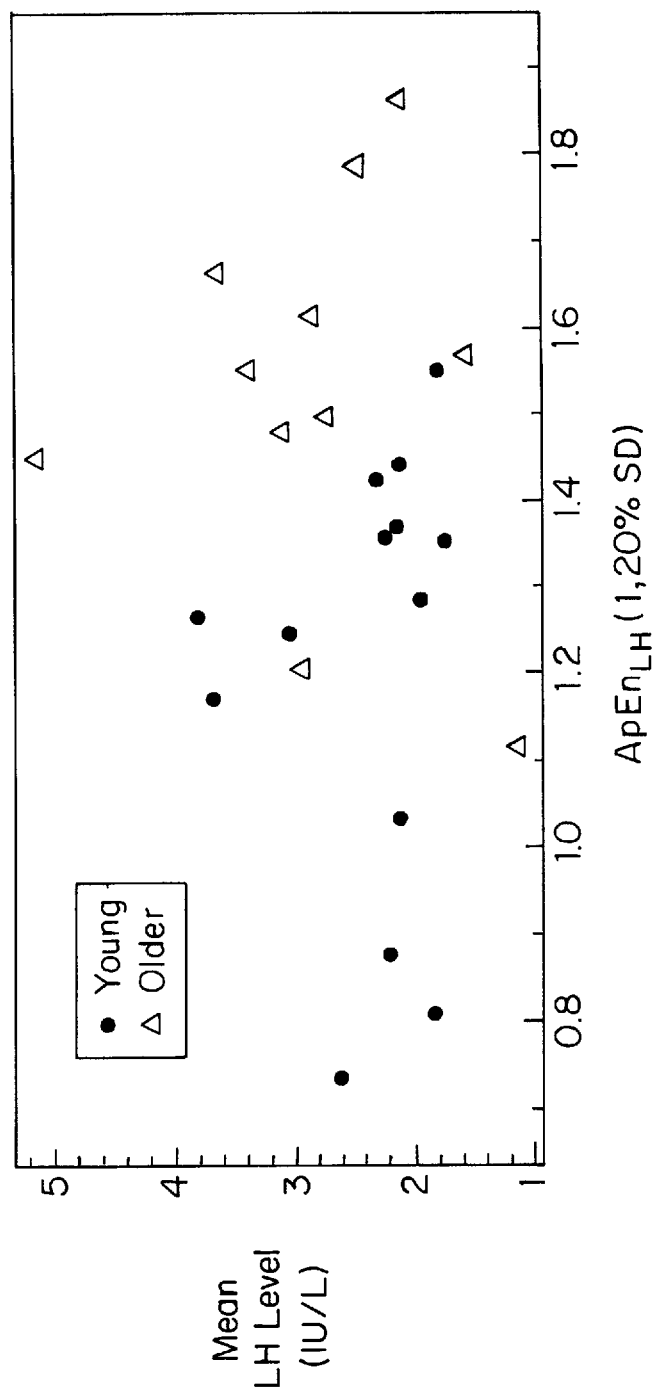

SYSTEM FOR QUANTIFYING ASYNCHRONY BETWEEN SIGNALS

RELATED APPLICATIONS

This application is a Continuation-In-Part of U.S. patent application Ser. No. 08/716,059 filed Sep. 19, 1996, (now U.S. Pat. No. 5,769,793, issued Jun. 23, 1998) which is a Continuation-In-Part of U.S. patent application Ser. No. 08/011,409 filed Jan. 29, 1993 (now U.S. Pat. No. 5,562,596 issued Oct. 8, 1996), which is a Continuation-In-Part of U.S. patent application Ser. No. 07/404,737 filed Sep. 8, 1989 (now U.S. Pat. No. 5,191,524 issued Mar. 2, 1993), the teachings of which are all incorporated herein by reference in their entirety.

BACKGROUND OF THE INVENTION

Diagnosis of many medical conditions requires the collection and analysis of medical data. In interpreting this data, doctors and other medical personnel have generally applied a number of rules of thumb, or qualitative assessments, to reach their diagnosis. These rules of thumb have proven to be quite useful but are not comprehensive, because certain ailments and abnormalities cannot be adequately identified merely by applying currently established rules of thumb.

One example where rules of thumb are applied is in monitoring electrocardiograph (EKG) data. EKG data is typically presented as a graphical output of a patient's heart activity. Doctors look for recognizable abnormalities and particular flags in the EKG data, as warning signals of health problems. They can discern certain abnormalities amongst this data by visually inspecting the graphical output; however, other important, more subtle abnormalities may go undetected. As such, the visual examination of data does not provide a complete diagnostic tool because some potentially significant abnormalities in the data are not apparent from visual inspection.

Another example of where rules of thumb are applied is in monitoring hormone secretion in an attempt to identify abnormal physiology. In the past fifteen years, endocrinologists have determined that episodic hormone secretion is a widespread phenomenon. The discovery of the link between abnormal pulsatility and certain hormonal disorders has prompted the recognition that a greater understanding of hormone secretion patterns, statistic to analyze hormone secretion data, and underlying system models could be of keen importance. To date, a number of pulse-identification algorithms have been developed to analyze hormone level data. These methods have been useful in detecting abnormal secretory patterns in some instances, and the expectation is that refined versions of these algorithms, applied to increasingly accurate and numerous data, will detect further abnormalities in hormonal secretion, earlier in the course of disease.

Another rule of thumb is used in fluid dynamics to design structures. Through experimentation, a force ratio between the inertial force and the viscous force of fluids has been developed. This ratio, or Reynolds number, is correlated with the formation of wakes when a fluid flows past an object. In systems with a fluid flowing at a fixed velocity and impinging on a rigid object, the wake behavior can be modeled. The Reynolds number cannot be easily used to model more complex systems.

For example, the Reynolds number cannot easily model a human heart because blood flow is not constant and the heart is not a rigid structure. The blood changes the heart surface dynamically and nonlinearly. Designers of artificial hearts rely heavily on trial and error, with the testing often being fatal. Artificial heart valves change the pattern of fluid flow in the heart, which creates areas of turbulence and areas of stagnation. Blood clots that form in the stagnation areas often find their way to the patient's brain, causing strokes.

SUMMARY OF THE INVENTION

The present invention concerns the quantification of a relative measure of patternness of a set of data. This data may be medical data or any other data for which it would be useful to know the relative measure of patternness present in the data. In determining the relative measure of patternness, subsets of data are first compared to determine the regularity and stability of similar patterns among the subsets. The detrimental effects of noise in these comparisons are minimized by the imposition of an imbedded algorithm. Intermediate values are then assigned to quantify the regularity and stability of similar patterns among the subsets that are compared. The output measure of patternness is based on the average of these assigned intermediate values. This measure is forwarded as an output signal to its destination.

In a preferred embodiment, the set of data is medical or other data, and the measure of patternness is a new information-theoretic measure called "approximate entropy," or ApEn. Moreover, the contribution of noise below a specified tolerance level to this measure is minimized as noted above.

A particular application for which ApEn may be valuable is in the analysis of electrocardiograph data such as beat-to-beat heart rate data derived from an EKG. When used in such an application, the R-R intervals between consecutive beats are first extracted from EKG data. These R-R intervals are a standard measure of the length of heartbeats. They are then averaged for a given length of time (preferably specified by the user) to produce a set of R-R interval averages. These averages are then analyzed as described above.

Another application for which the application of ApEn may be valuable is in the analysis of hormone secretion behavior, measured typically from blood samples. Pulsatile secretions are found in many hormones, so there is great potential for this measure to identify deviations from normal secretion patterns, and to identify diseases pre-onset of symptoms. The input data for patternness analysis in this case is a series of blood level measurements of a specified hormone.

The present invention may also be used with other types of medical data. For instance, it may be used with electro-encephalograph data, electro-ocolgram data, electro-myogram data, and respiratory measurement data. To analyze data via the present invention, it is often necessary to first convert the data into digital form before processing it.

The present invention may also have significant non-medical applications. It may be used to analyze stock market data, such as the Dow Jones index, individual stock prices, and bond prices over time. It may also be used to analyze aerodynamic, hydrodynamic, and astronautic data, such as velocities, momenta, pressure, position data, etc. and especially to provide a figure-of-merit for turbulent behavior of these data. The processing of the data is carried out by a data processing system. The data processing system should include a comparator for performing a comparing step in which contiguous runs of data of a prescribed length are compared to a plurality of other contiguous runs of data of the same length to determine measures of regularity and stability. The measure of stability should also act as a filter to remove noise substantially below a specified tolerance level. The processor aggregates these regularity and stability measures to generate a single number as an approximate entropy value, ApEn.

The approximate entropy value may be forwarded to a number of different output peripheral devices. For instance, the approximate entropy value may be output to an alarm that signals when the approximate entropy value lies outside a safe range. In addition, the approximate entropy value may be employed with a meter that displays the approximate entropy value, as well as with an automated adjustor that automatically reacts in response to the approximate entropy value. The response performed by the adjustor includes adjusting an external stimulus by dispensing medication, performing medical procedure, or disrupting a flow stream. Further, a storage device may be attached to the data processing system to record the approximate entropy value over a period of time.

The system may be used to control the flow of a medium across or through a region constrained by a primary solid. The primary solid partially interferes with the flow of the medium. The system comprises at least one sensor, a processor, a compensated negative feedback control, an actuator, and a secondary solid. The sensor is located in proximity to the primary solid to measure and quantify a flow parameter of the medium. The processor is coupled to the sensor to determine a time-varying measure of relative patternness for the medium in proximity to the primary solid. In particular, the measure of relative patternness is quantified by approximate entropy. The negative feedback control is coupled to the processor and generates a time-varying control signal in response to the time-varying measure of relative patternness. An actuator is coupled to the negative feedback control to produce a driving force in response to the control signal. The actuator urges a secondary solid to affect the flow characteristics of the medium in proximity to the primary solid.

In particular, a flow control system is used to control fluid flow to optimize turbulence in the medium. The sensor measures flow parameters such as speed, pressure, and direction of flow. In response, the actuator urges motion in the secondary solid, such as a constrictor, flap, or vibrating plate. The secondary solid interferes with the wake caused by the primary solid.

Furthermore, the system can be used to assess deoxyribronucleic acid (DNA) sequences. A DNA sequence from an automated DNA sequencer can be evaluated using an ApEn computer. Such a system can automatically detect altered genes and evaluate the accuracy of DNA sequences. For example, a DNA sequencer embodying the invention can automatically read sequencing gels and produce an accurate DNA sequence listing.

Although ApEn is useful for measuring the amount of patternness in a single series of data, the human body and other interconnected systems are more accurately modeled as a network of signals. As such, the amount of patternness in a single parameter is not necessarily indicitive of the underlying state of the network. To analyze the network, per se, a preferred embodiment of the invention employs cross-ApEn to quantify the amount of asynchrony or conditional irregularity in interconnected networks.

A preferred embodiment of the invention is a data processing environment which processes a plurality of signals to detect a system state, such as typicality or atypicality. In accordance with a preferred embodiment of the invention, a first and a second set of time-series data points are provided from an overall system being examined. In a particular preferred embodiment, the overall system is a living biosystem and the time-series data are biological parameters. The overall system can instead be a financial market, where the time-series data are values of market indicators. Furthermore, the overall system can be an electromechanical system, where the first and second signals are parameters of the electromechanical system.

The processor operates on the first and second sets of data points by defining a first and a second class of contiguous runs of a prescribed length of the first and second set of data points, respectively. The processor then assigns quantitative values to measure the regularity of similar patterns between the first and second sets of data points from the defined classes. These assigned quantitative values are aggregated to quantify asynchrony between the first and second signals. In either case, the data points can be sampled from the time-series data at different frequencies and at different times as long as a consistent protocol is used to measure asynchrony.

The above and other features of the invention, including various novel details of construction and combination of parts, will be more particularly described with reference to the accompanying drawings and pointed out in the claims. It will be understood that the particular system for quantifying asynchrony in an interconnected network embodying the invention is shown by illustration only and not as a limitation of the invention. The principle and features of this invention may be embodied in varied and numerous embodiments without departing from the scope of the invention.

BRIEF DESCRIPTION OF THE DRAWINGS

FIGS. 2A–B show sample sets of data.

FIGS. 4A–C show three different sample sets of data.

FIGS. 15A–15B are representative serum hormone concentration time-series of LH and testosterone data, respectively, for an aged subject.

FIGS. 16A–16B are scatterplots of mean LH level vs. ApEn(LH) and of mean testosterone level vs. ApEn (testosterone), respectively.

DETAILED DESCRIPTION OF PREFERRED EMBODIMENTS OF THE INVENTION

A preferred embodiment of the present invention concerns the determination of a relative measure of patternness in sets of data, especially sets of medical data. In particular, a data processing system 2 is utilized to produce a single number measuring the relative measure of patternness in a set of medical data, such as electrocardiograph (EKG) or hormone secretion data. This single number constitutes a measure of regularity or "complexity," which is an approximate entropy value in the data derived from the set of medical data, and will be referred to hereinafter as approximate entropy or ApEn. It is useful in determining, from the set of medical data, both the well-being of the data producing organ, or other part of the body, and the general well-being of the individual. It is also useful in other applications that will be discussed below.

Figure 1:
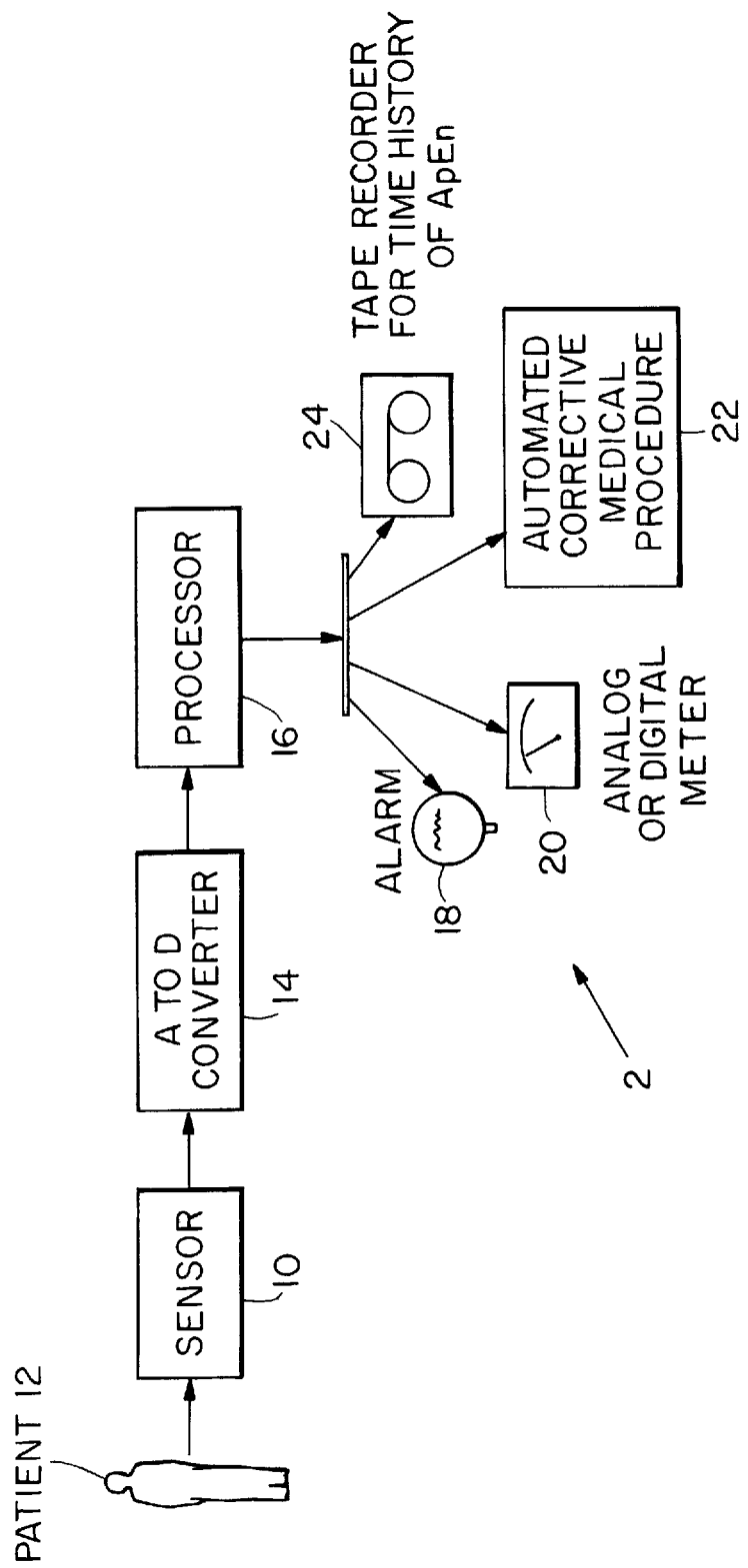
FIG. 1 shows a data processing system that calculates an approximate entropy value and acts on the calculated value.

FIG. 1 shows the major components of the data processing system used to obtain this approximate entropy value. Specifically, a sensor 10 is applied to a patient 12 to obtain medical data. Techniques for applying such a sensor 10 are well known in the prior art. Once the sensor 10 is appropriately attached to the patient 12, the sensor begins receiving data relating to the patient's system. This data is typically received in analog form and may be output as a graph, known as a tracing.

Although the analog medical data is useful as a graphical representation of the data, it is difficult to process. Hence, the present system includes an analog to digital converter 14 that samples the analog waveform of the medical data tracing to produce a digital representation of the samples. This digital representation is then forwarded to a processing engine 16 wherein the digital data is processed to produce the approximate entropy measure.

The system extracts data intervals from the set of medical data and averages them for a given, user-specified short length of time to produce an average set of data intervals. This average set of data intervals is processed to obtain the approximate entropy measure. The user can choose to work with the data intervals directly too. The processing engine 16 contains the appropriate software to perform the necessary calculations to obtain the approximate entropy measure. This software can be written in any of a variety of high level languages such as Fortran, C, Pascal, etc. The details of the software will be discussed more below.

The resulting approximate entropy measure as computed by the processing engine 16 can be output to a number of different types of peripheral devices. For instance, the approximate entropy measure can be forwarded to an alarm 18 which indicates when the measure lies outside an acceptable range. Further, the approximate entropy measure can be forwarded to an analog or digital meter 20 that shows the current value of the measure as computed by the processing engine 16. Still further, the approximate entropy measure can be sent to an automated corrective medical procedure device 22. Such a device 22 automatically reacts to remedy a difficulty noted by an unsatisfactory approximate entropy measure. For example, if the approximate entropy measure indicates a low level of a vital hormone, the automated corrective procedure device 22 can excrete a given quantity of the hormone in response to the low approximate entropy measure.

Another alternative is for the approximate entropy measure to be recorded on a tape recording or other recording devices 24 such that a time history of the approximate entropy measure is kept. Each of these peripherals 18, 20, 20, 22 and 24 need not exist in isolation. The system can be configured such that all of these devices are connected simultaneously to the processing engine 16. Moreover, peripheral devices other than those described can be attached to the processing system. These suggested devices are not meant to be exhaustive of the personal devices that lie within the scope of the present invention.

Such a measure of patternness of a set of time-series data is especially useful in medical applications. Medical personnel have for years visually examined hard copies of medical data presented in graphical form to attempt to discern abnormalities in the data. Such efforts, however, can only discern patternness at a superficial level that lacks the usefulness and completeness of the measure of the present invention. Moreover, past efforts have not been able to distill the patternness into a single comprehensive measure that is both readily usable and robust to noise.

The present invention can be used with medical data such as electrocardiograph (EKG) data, electroencephalogram (EEG) data, electro-oculogram (EOG) data, electromyogram (EMG) data, and respiratory data such as ventilation pulses that measure tidal volume. It can also be used to analyze the patternness and pulse stability exhibited in hormone secretion. Further, it can be used to analyze non-medical data, such as stock market data over time; and aerodynamic, hydrodynamic, and astronautic data, to provide a figure-of-merit for turbulent behavior of these data. This list is not intended to be exhaustive of the potential applications of the present invention; rather it is merely intended to be illustrative. The present invention can, in fact, be useful anytime wherein knowing a relative measure of patternness in a set of data is useful.

The historic development of mathematics to quantify regularity has centered around various types of entropy measures. Entropy, in a different context, has been an integral part of the modern quantitative development of thermodynamics, statistical mechanics, and information theory. Although, intuitively, the entropy quantifications in physics address the issues of randomness and regularity, the equations themselves involve integrals and derivatives of known functions, such as work, temperature, and energy (Feynman, R. P., *The Feynman Lectures on Physics*, Vol. 1, Reading:Addison-Wesley, 1963:44.10–44.13). In modern probability theory, entropy is explicitly defined, given a probability distribution (measure) for elements of a set (Billingsley, P., *Ergodic theory and information*, New York:Wiley, 1965:60–94). This definition coincides with intuition in that systems having more random probability distributions have greater entropy. Nonetheless, these approaches to entropy definition are not directly applicable to time-series data analysis.

Kolmogorov-Sinai (K-S) entropy (Eckmann, J. P., and D. Ruelle, "Ergodic Theory of Chaos and Strange Attractors," *Rev. Mod. Phys.* 57(3) (July 1985):617–656) generalizes the probabilist's definition of entropy, in a theoretical setting, and paves the way to entropy equations for time-series data, as discussed below. There has been particularly keen interest in the development of these equations in the last 10 years, since entropy has been shown to be a critical "summary" statistic in nonlinear dynamical system analysis and chaos (Crutchfield, J. P., and N. H. Packard, "Symbolic Dynamics of One-Dimensional Maps: Entropies, Finite Precursor, and Noise," *Int. J. Theor. Phys.* 21 (1982):433–465). In 1983, Grassberger and Procaccia developed an equation, based on the K-S entropy, to measure the entropy of a time series (Grassberger, P., and I. Procaccia, "Estimation of the Kolmogorov Entropy From a Chaotic Signal," *Phys. Rev.* A 28 (1983):2591–2593); this equation, and a slight variation produced by Takens (Takens, F., "Invariants Related to Dimension and Entropy," in *Atas do* 13, Rio de Janeiro: Col. Brasiliero de Matematicas, 1983), have become the "standard" entropy and regularity measures for use with time-series data.

The method for ApEn is somewhat similar in appearance to two algorithms that estimate the Kolmogorov-Sinai entropy, given by Eckmann and Grassberger. Approximate entropy has three technical advantages in comparison to Kolmogorov-Sinai entropy for general statistical usage. Kolmogorov-Sinai entropy is badly compromised by tiny amounts of noise, generally requires a vast amount of input data to achieve convergence, and is usually infinite for random processes. Approximate entropy is nearly unaffected by noise of magnitude below "r," gives meaningful information with 1000 points, and is finite for both random and deterministic processes. This last item allows ApEn to distinguish versions of random processes, reasonable candidates for general medical processes including heart rate models, from each other, whereas Kolmogorov-Sinai entropy would be unable to do so.

ApEn provides a widely applicable equation for the data analyst that will distinguish data sets by a measure of regularity. The intuition motivating ApEn is that if joint probability measures for reconstructed dynamics that describe each of two systems are different, than their marginal distributions on a fixed partition are likely different. In contrast, the K-S entropy was developed by Kolmogorov to resolve the theoretical mathematical question of whether two Bernoulli shifts are isomorphic, and is primarily applied by ergodic theorists to well-defined transformations, with no noise and an infinite amount of "data" available.

There are several indication that the approximate entropy measure may detect a broad range of problems in the human body heretofore undetected. It has recently become known that much of the human body exhibits possibly chaotic, and random behavior when functioning properly. As noted in James Gleick, *Chaos: Making a New Science* (New York-:Penquin Books, 1987:275–300)(summarizing numerous primary sources), a change in the nature of this normally irregular behavior may be a signal that problems exist. Unfortunately, the changes in this irregular behavior usually are not readily discernible by visual review of the data that measure the body's function (EKG, EEG, etc.). Approximate entropy provides a measure for discerning (subtle) changes in the degree of the irregular behavior exhibited, and hence in identifying improper body function.

The ability of approximate entropy to directly measure feedback system change in many systems may allow this measure to predict ailments in the human body pre-onset. Many systems of the human body exhibit coupled, or feedback behavior when functioning properly. For example, the male reproductive system can be viewed as a feedback loop. Specifically, the hormone LHRH determines LH production, which determines testosterone production, and the testosterone production, in turn, determines LHRH production. The heart, consisting of the sinoatrial node and the atrioventricular junction, is another example of such a coupled feedback mechanism. Changes in this feedback loop, either in extent or in nature, may cause or indicate disease.

Changes in feedback are often reflected in corresponding changes in the regularity of systems. Decoupling and lessening feedback is explicitly noted by decreasing approximate entropy in the system. This barometric property of entropy may have two important medical implications. First, it may allow for the identification of insidious diseases not otherwise detectable, pre-onset of symptoms, and second, it may help to identify the physiologic system change that is the cause of some diseases.

The approximate entropy measure is somewhat similar in appearance to an algorithm provided by Eckmann et al. for the Kolmogorov-Sinai (K-S) entropy which can be expressed mathematically as:

$$\text{Entropy} = \lim_{r \to 0} \lim_{m \to \infty} \lim_{n \to \infty} [\Phi^m(r) - \Phi^{m+1}(r)] \tag{1}$$

Equation 1 is disclosed in Eckmann, with $\Phi$ as given therein. Unfortunately, Equation 1 has little general practical utility, for two reasons. First, accurate entropy calculations for most data sets cannot be performed in "finite" time; that is less than multiple of years of computer time per calculation. Part of the difficulty in calculating K-S entropy lies in that it is a triple-limit and that the computational time to ensure accuracy grows exponentially with m. Second, Equation 1 degrades badly (disintegrates) when noise is present because the presence of noise in the data causes the entropy calculation to explode to very high values. With Kolmogorov-Sinai, entropy noise considerations dominate other system characteristics. Therefore, it has proven to be a measure that lacks robustness. The present invention, in contrast, overcomes these difficulties, and provides a relative measure of patternness that is both readily calculated for any time-series data and robust to noise.

The basic approach of the method of the present invention is to compare contiguous runs of the data, so as to look for patterns amongst the subsets. All groups of contiguous subsets of the data are compared against each other, in search of the proportion of similar patterns for each "template" pattern. The approximate entropy measure is derived from an average of these proportions.

A step-by-step computation of approximate entropy will next be explained for the preferred embodiment. The computation is performed for the example series of data given in FIG. 2A, a "perfectly patterned" series of alternating 0's and 1's. A more mathematically formal description of the preferred embodiment follows.

FIG. 2A shows an example series of data that is useful in explaining the mechanics of calculating the approximate entropy measure. In this preferred embodiment, the processing engine 16 receives such a series of data and begins processing it. Two system parameters are set before the processing engine 16 calculates the approximate entropy measure. These parameters can be either encoded in the software or requested from the user of the system. These parameters include a value r, which stands for radius, and is a filter factor, and a value m which is the length of a run or template pattern length. Defining these variables as fixed is quite different from what is done with K-S entropy, for K-S entropy is calculated as a limiting value as these variables approach zero and infinity, respectively. Moreover, the number of elements in the set of data is fixed in the present invention. K-S entropy, on the other hand, requires that the number of elements approaches infinity. The significance of these parameters will be discussed in more detail below. It is the fixing of the two parameters, m and r, that provides the general practical utility of the preferred embodiment of approximate entropy.

Figure 3:
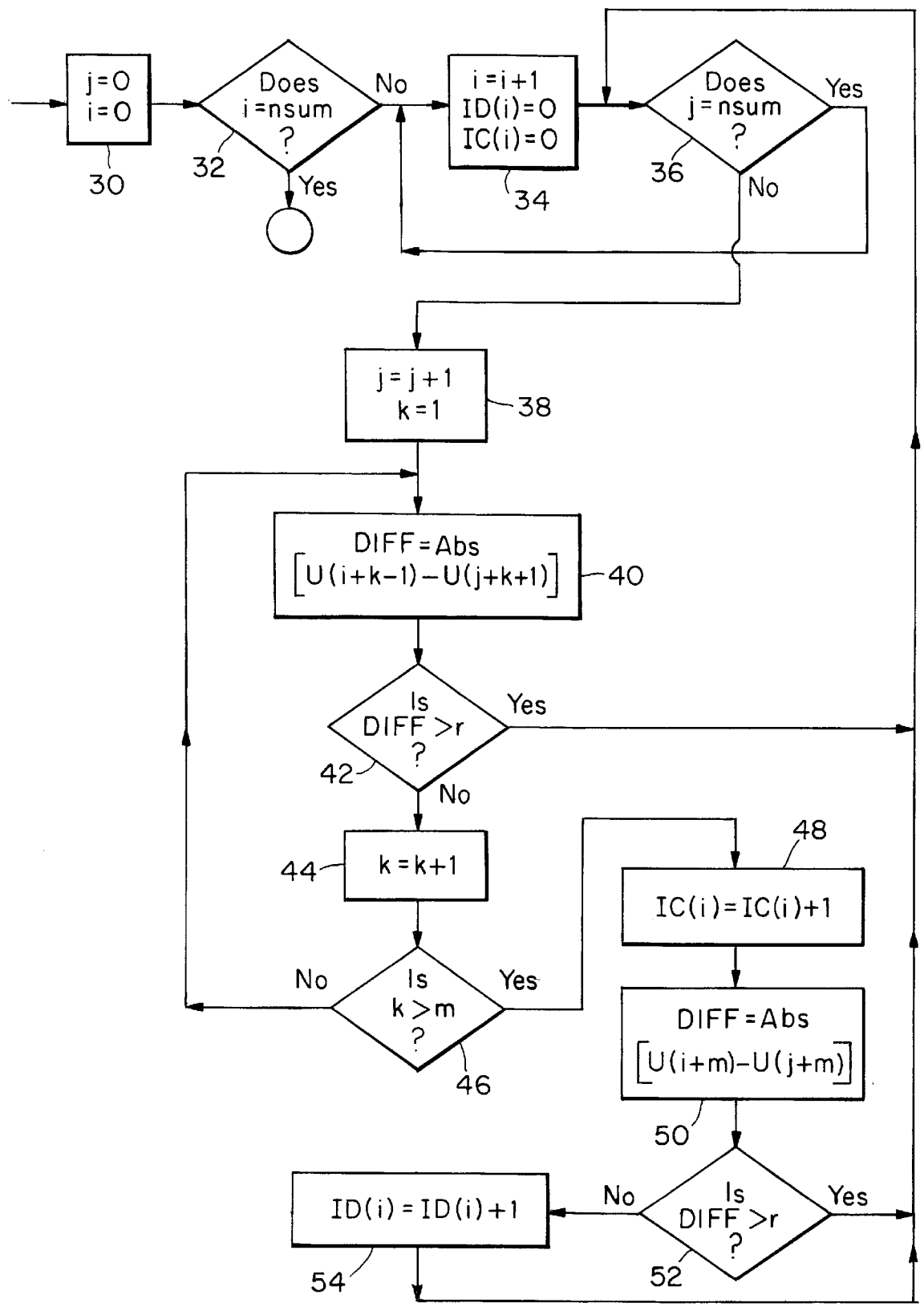
FIG. 3 shows a flow chart of calculating a measure of approximate entropy.

Having set these parameters, the present invention proceeds to perform the necessary calculations to compute the approximate entropy measure. The processing engine 16 begins by following the steps illustrated in FIG. 3. The numerical data are given as U(1), U(2), ..., U(nsum). The steps performed by the processing engine 16 are performed primarily within a loop where the index of the loop, i, goes from one to the number of elements in the set of data (denoted as nsum) as indicated by steps 30, 32 and 34. At the beginning of this loop, the first locations in two memory arrays are set at a value of zero (the two memory arrays ID(i) and IC(i)). Nested within the larger loop is a smaller loop that has a loop index, j, that also goes from 1 to nsum (steps 30, 36 and 38).

The main part of this method involves calculations to appropriately fill the arrays ID(i) and IC(i), for i=1, 2, ..., nsum. The final calculation of the approximate entropy follows in a straightforward manner from all these ID and IC values, as discussed below.

Within the inner loop, the variable k is set initially at a value of 1 (step 38). To keep track of the locations of comparisons k is used within this inner loop as a counter. Next, the value of the variable DIFF is calculated as the absolute value of the difference U(i+k-1)–U(j+k-1) (step 40). The variable DIFF is equal to the absolute value of the difference between the elements within the sets of data that are currently being compared. Once DIFF is calculated, the system checks to see whether DIFF is greater than r (step 42). The system, in other words, checks to see whether U(i+k-1) lies within a distance less than the radius (tolerance level) from U(j+k-1). If DIFF exceeds the radius, j is incremented (step 38). However, if the difference is less than or equal to the radius, k is incremented (step 44). In the event that k is incremented, the system checks to see whether k is greater than m (step 46). This comparison is to check whether the value being examined lies within or outside the run (or window) length currently being compared as designated by m. If k is not greater than m, then DIFF is recalculated using the new value of k (i.e. step 40 is repeated with the new k). The new value of k shifts the comparison over by one element. For instance, if U(1) and U(2) had been initially compared after k was incremented, DIFF is recalculated between U(2) and U(3).

Suppose, in contrast, that k is greater than m (step 46). In that case, the array location at IC(i) is incremented by 1 (step 48). Furthermore, DIFF is recalculated to equal the absolute value of U(i+m)–U(j+m) (step 50). This calculation is to determine whether the corresponding elements located a run length away from the elements that were just compared are also close enough for their difference to lie within the radius. Step 52 checks to see whether this difference lies within the radius. If the difference is not greater than the radius, the array location ID(i) is incremented by 1 (step 54). If the difference is greater than the radius, only the value of j is incremented by 1. The steps are repeated until both i and j equal nsum.

For illustrative purposes, suppose that the system processes the data shown in FIG. 2A. Further suppose that m=2 and r=0.5. In the first iteration of the steps shown in FIG. 3, i=1 and j=1. Hence, the difference is calculated as the difference between U(1) and U(1) (step 40). This difference is zero which means that the difference is less than the radius 0.5 (as checked by step 42). As such, k is incremented by 1 (step 44). However, k, is not greater than m (i.e. 2) (step 46); thus, DIFF is recalculated (step 40). This subsequently evaluated value of DIFF is derived by comparing U(2) and U(2). In making that comparison, DIFF is again 0 (step 42).

After incrementing k (step 44), k is greater than m (step 46), so IC(1) is incremented (step 48) from 0 to 1. Then DIFF is recalculated (step 50) between U(3) and U(3), and because DIFF=U(3)–U(3)=0, ID(1) is incremented by 1, from 0 to 1 (step 54).

Once ID(1) has been incremented, the value of j is also incremented (step 38) to j=2. The result is that DIFF is next calculated between U(1) and U(2) (step 40). Because the absolute value of DIFF is greater than the radius (1 is greater than 0.5), the value of j is incremented once again.

With j having a value of 3 and i having a value of 1, the system sets the value k at 1 (step 38), and it then computes the absolute value of the difference between U(1) and U(3) (step 42). Because both U(1) and U(3) are equal to 1, the difference between them equals zero. The difference lies within the radius (see step 42), and k is incremented to have a value of 2 (step 44). The system then compares k with m and determines that k is not greater than m. It subsequently recalculates the value of DIFF using the incremented value of k (i.e. 2). The system compares U(2) with U(4) to produce a DIFF value (step 40). This value of DIFF is checked in step 42 and equals zero and accordingly, is not greater than r. Then k is incremented again (step 44), but this time, k is greater than m. With k being greater than m (as checked in step 46), step 48 is performed which increments the value at IC(1) from 1 to 2. The value of DIFF is recalculated for the corresponding values a subpattern length away from the most recently compared values (step 50). In the current case, U(3) is compared with U(5). This difference is not greater than r (see step 52); so, the value at ID(1) is incremented from 1 to 2.

Once ID(1) has been incremented, the value of j is also incremented (step 38). The result is that DIFF is calculated between U(1) and U(4) (step 40). Because the absolute value of the difference is greater than the radius, the value of j is incremented once again. With j having a value of 5, the comparison between U(1) and U(5) computes a DIFF value, equal to zero (step 46), that is within the radius (step 42). The values at U(2) and U(6) are next compared. Because the absolute value of the difference (equal to zero) is less than or equal to the radius (step 42) and k is greater than m (see step 46) after being incremented, the value at IC(1) is incremented from 2 to 3 (step 48). Furthermore, DIFF is calculated, but it is calculated between U(3) and U(7) (step 50). This absolute value of the difference is less than the radius (i.e. equal to zero as checked in step 52). As a result, the system increments the value at ID(1) from 2 to 3 (step 54). This entire process is repeated until j equals 10 which is the nsum value for the current example. At this point, the ID(1) and IC(1) computation is concluded; both ID(1) and IC(1) equal 5. The process is then repeated with i set at 2 as opposed to 1, and it is further repeated for the remaining values of i up to nsum. For this example, at the end of the computation, each element of the ID and IC arrays has the value 5.

The above described process basically compares contiguous subsets or subpatterns of the data. It first chooses a value at U(i) and finds a U(j) for which the difference between U(i) and U(j) is within the radius, r. Because, in the example, the radius is 0.5 and the example has only integer values, U(i) and U(j) must be identical to lie within the stated radius. Hence, by comparing U(i) with U(j), the system checks for those values in the data that are identical to U(i).

Once an identical value is found, the system checks the next values in the respective subpatterns of data of the values that were just compared to see if they are also identical.

When i equals 1 the first subpattern of data is comprised of U(1) and U(2). In the example case, U(1) and U(2) are not identical so U(1) is compared with U(3). This comparison reveals that they are identical. The system as described above then compares the next value in the respective subpatterns: U(2) and U(4). In the above described example these two are identical; hence, the matrix location IC(1) is incremented. IC(1) keeps track of the number of subpatterns identical to the subpatterns that start at U(1). The system, however, performs an additional type of comparison. It also wants to see if the next value that succeeds the subpattern containing U(i) is identical to the next value that succeeds the subpattern containing U(j). If those values are identical, the counter memory location ID(i) is incremented. ID(i) can, thus, fairly be said to check for an additional level of patternness in the data.

When both of the loops have been completed the arrays IC(i) and ID(i) have been fully created. Each location contains the number of matches for each respective i value. The system utilizes these arrays to calculate a ratio which is determined for each i. The ratio equals the ID(i) value divided by the IC(i) value. The logarithm of the ratio is then taken for each i, and the resulting logarithms are summed. This sum is divided by the number of data values (i.e. nsum). The resulting value is equal to the average of the logarithms of the ratios. To produce a positive result, the average is multiplied by −1 to produce the approximate entropy measure.

This calculation determines the appropriately averaged relationship between the ID(i)'s and the IC(i)'s for all i. Heuristically, approximate entropy measures the (logarithmic) likelihood that runs of patterns that are close remain close on next incremental comparisons. The IC(i)'s measures the regularity (or frequency) of similar patterns; the ID(i)'s measure the stability of these patterns upon incrementing.

The calculation of the approximate entropy measure in the example case of FIG. 2A produces a value of zero. The data in FIG. 2A are completely patterned so the ratio of IC to ID equals 1, for every i, and the log of one equal zero. Thus, the approximate entropy measure equals the sum of a number of zeroes, or zero. In this example, the approximate entropy measure appropriately validates the intuitive conclusion: the completely patterned data produces an approximate entropy value of zero. In contrast, if the data is completely random, and given by white noise, the approximate entropy approaches infinity (as nsum approaches infinity).

FIG. 2B shows an "intermediate" example set of data. In this data set, every third slot is preset, with alternating values of 1 and 0 (U(3)=1, U(6)=0, U(9)=1, U(12)=0, . . . ). All other slots have either 0 or 1 in them such that the value a slot has is randomly chosen, probability ½ of either 0 or 1. A computation can be performed similar to the one performed above for the example illustrated in FIG. 2A. For set parameter values of m≧3 and r<1, the approximate entropy of the sequence is computed to equal (⅔) ln (2). This result is again consistent with intuition, in the following sense. The approximate entropy (⅔) ln (2) is greater than 0, and the sequence in FIG. 2B appears more random, and less patterned than the sequence in FIG. 2A (which yielded the approximate entropy value of 0). In contrast, the sequence in FIG. 2B has a certain measure of patternness, given by the alternating 0's and 1's in every third location. One would expect the sequence to have lower approximate entropy than the sequence consisting entirely of random 0's and 1's in all slots. Indeed, this lastly defined sequence has approximate entropy equal to ln (2), larger than (⅔) ln (2), again confirming intuition. The consistency of the approximate entropy equation with intuition is another important property of this new measure for practical utility.

The above analysis can readily be expressed in mathematical terms. To express the method in such terms, let the input data be a time series denoted as U(i) where i is an index of time that goes from 1 to N. From the U(i), sequences of vectors X(i) are defined by setting X(i)=[U(i), . . . , U(i+m−1)] where m equals run or subpattern length. In the example illustrated in FIG. 2A, X(1) equals [U(1), U(2)], X(2) equals [U(2), U(3)], etc. The vector sequence X(i) can be thought of as the previously discussed runs used in the comparisons. Let $C_i^m(r)$ equal the number of X(i); such that the difference between X(i) and X(j) is less than or equal to the radius r, divided by the number of vectors in the data, N−m+1. The difference between the vectors X(i) and X(j) is defined as the maximum of the differences of their respective scalar components. $C_i^m(r)$, thus, counts the number of runs that match (i.e. fall within the tolerance) and divides this number of matches by the number of vectors. Knowing $C_i^m(r)$, one then defines $\Phi^m(r)$ as $$\Phi^m(r) = (1/N - m + 1) \sum_{i=1}^{N-m-1} \log C_i^m(r). \quad (2)$$

From Equation 2, it is clear that $\Phi^m(r)$ is equal to an average of the logarithms of the $C_i^m(r)$ for i=1, . . . , N−m+1.

The approximate entropy measure is defined as:

$$\text{approximate entropy} = \Phi^m(r) - \Phi^{m+1}(r) \quad (3)$$

where m, r and N are all fixed. From the previously disclosed equations, the approximate entropy measure can be rewritten by substituting equations for the $\Phi$'s such that $$ApEn = \frac{1}{N - m + 1} \left( \sum_{i=1}^{N-m+1} \log C_i^m(r) - \log \cdot C_i^{m+1}(r) \right). \quad (4)$$

Equation 4 yields a single value for approximate entropy. The value is in the range of zero to infinity. An approximate entropy equal to zero indicates that the system is completely patterned. An approximate entropy value greater than zero indicates that the system is somewhat unpatterned. Further, higher values of ApEn imply lesser degrees of patternness. Thus, the present invention allows one to compare sets of data to determine which exhibit a greater degree of patternness.

The ApEn equation requires that two input parameters, m and r, be set; m is the "length" of compared runs, and r is effectively a filter. It must be emphasized that m and r are fixed for a given application of ApEn. ApEn values can vary significantly with m and r for a given system. A valuable property of ApEn is that it is finite for stochastic processes, whereas K-S entropy is usually infinite; thus ApEn can potentially distinguish versions of stochastic processes from each other, while entropy would be unable to do so.

Most important, despite the apparent similarities between ApEn and the K-S algorithm, ApEn is not intended as an approximate value of Kolmogorov-Sinai entropy. It is essential to consider ApEn as a family of statistics; system comparisons are intended with fixed m and r. For a given system, there is usually significant variation in ApEn over the range of m and r. Furthermore, ApEn is a biased statistic; the average value of ApEn increases with increasing N. Thus for controlled comparisons between two groups, N must be fixed.

As mentioned above, it is crucial, in developing a patternness measure, to produce an equation that is both computable in finite time and robust to the contribution of noise. The fixing of m, the run length or length of a template pattern, as a small integer value, insures computation in finite time in the present invention. The robustness is obtained by careful choice of a value of the radius or tolerance level (r). In choosing r one must consider that noise can dramatically affect the resulting computation if r is chosen too small. In K-S entropy, the entropy is calculated as r approaches zero and, as such, noise dominates the computation, adding significantly to the level of entropy that is measured. In the present invention, the radius r is fixed so as to minimize the effects of the noise in the data on the computation. Specifically, noise well below r has negligible effect on ApEn. It should be reemphasized, however, that r provides ApEn as a relative measure of patternness at a prescribed tolerance level.

FIG. 4 illustrates a comparison of the effects of using approximate entropy on different waveforms as opposed to established measures. Suppose that the data sought to be analyzed ideally represents a discrete sampling from a perfect sine wave as shown in FIG. 4A. Suppose, however, that a small amount of noise corrupts the data as in FIG. 4B. The effect of this noise on an established entropy calculation is great. It dramatically alters the result. The mean and standard deviation are hardly affected, nor is the approximate entropy measure significantly affected. Suppose, however, that the data is like the data shown in FIG. 4C with large errors. The mean and standard deviation are greatly affected. Both entropy and approximate entropy are, in contrast, nearly unaffected. Thus, the present invention obtains the best aspects of both types of established measures.

The input data for ApEn is a scalar time-series, with typically between 100 and 5000 numbers. Fewer than 100 numbers will likely yield a less meaningful computation, especially for m=2 or m=3. Values of m=1, 2 or 3 are generally chosen.

The present invention filters out the noise by choosing a value of r such that the contribution of noise to the entropy calculation is minimized. A balance is sought in choosing r. If r is too small, noise will corrupt the approximate entropy calculation. If r is too large, too much "fine detail" will be lost to the coarseness of the filter. A range for r that appears to be desirable, and that has performed well in studies such as the neonatal study described earlier, is $0.1\sigma$ to $0.25\sigma$ where $\sigma$ is a standard deviation of the data. These values of r are usually effective in distinguishing data sets. Noise in the data much smaller than r is effectively filtered out in the ensuing calculation.

Heartbeat Data

Figure 5:
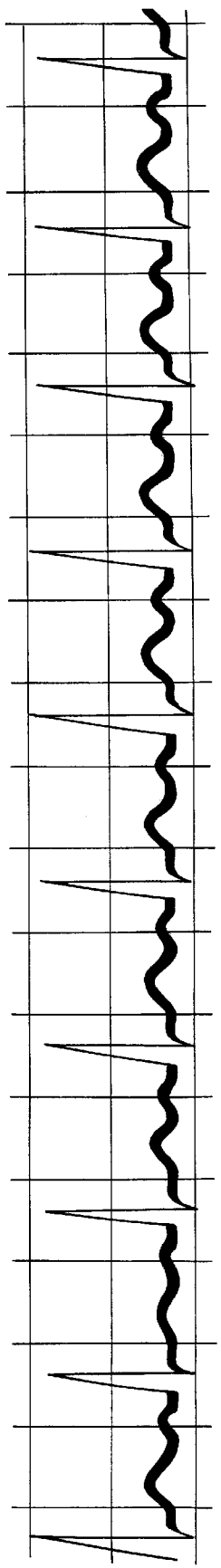
FIG. 5 shows a sample EKG tracing.
Figure 6:
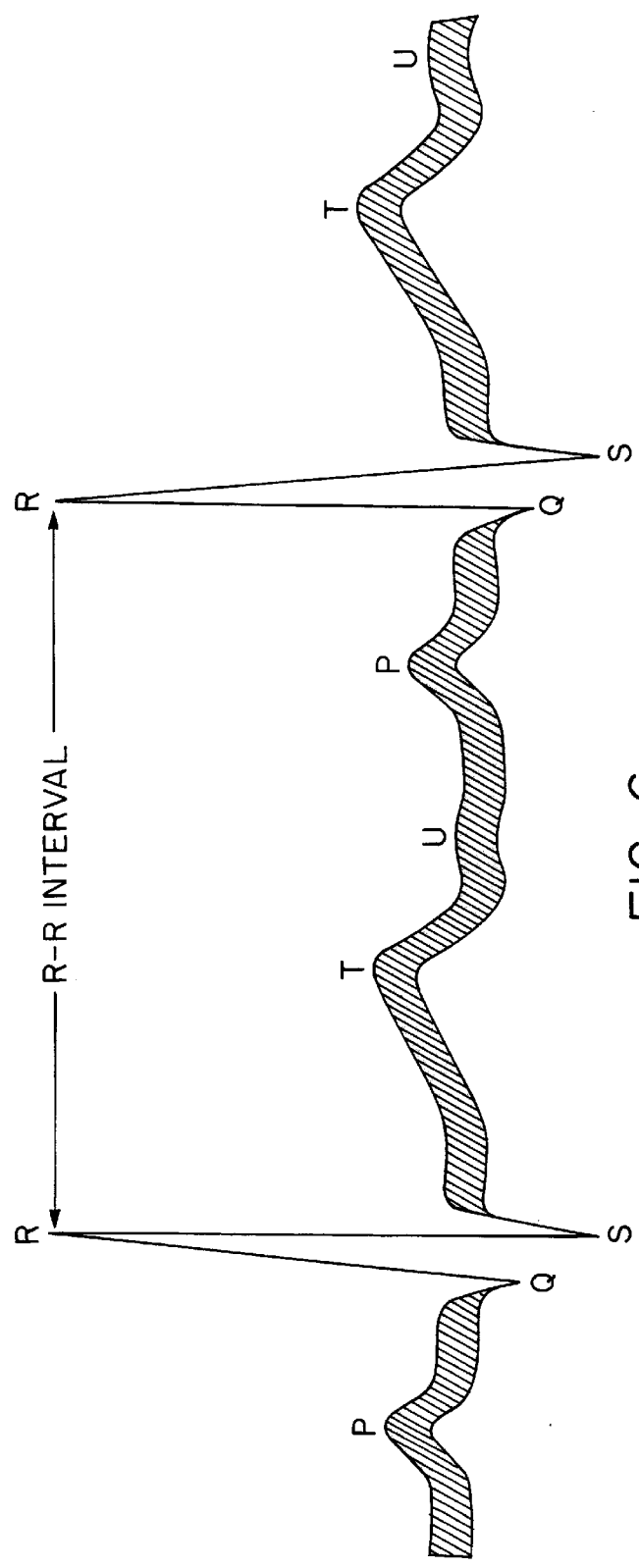
FIG. 6 shows two sample pulses of a heartbeat.

Approximate entropy, applied to heartbeat data, can potentially be used as a general barometer of human health. In particular, the data processing system looks at the interbeat intervals in EKG tracings. FIG. 5 shows a typical EKG tracing for a healthy heart. The interbeat intervals are measured between the R-portions of consecutive pulses. Two consecutive pulses, and the R—R interval for them, are shown in FIG. 6.

Approximate entropy has already been found to distinguish sick neonates from healthy neonates in a study conducted by one of the inventors at the Yale University School of Medicine. In this study, performed with two faculty pediatricians, data were taken for 15 healthy neonates and 9 asphyxiated neonates. Their heart rates were averaged every 5 seconds, for 1000 measurements. The approximate entropy was lower for the sick group, as anticipated, corresponding to greater patternness. The sick group had an approximate entropy average of 0.80±0.31 versus 1.22±0.12 (mean±1 S.D.) for healthy neonates. The significance of this result was p=0.003 (t-test). Comparisons between the two groups, using the clinically used measure of heartbeat variability, VAR (standard deviation) did not show a significant difference between the two groups (p=0.14). Tables 1a and 1b show the data from this study for both the healthy and sick groups, respectively. Moreover, a serial study on a septic infant with persistent pulmonary hypertension showed a large steady increase in approximate entropy with recovery, further confirming approximate entropy as a barometer of general health. Additionally, approximate entropy discerned the poor health of several of the infants who were otherwise without recognizable EKG abnormalities.

Moreover, ApEn is useful in monitoring fetal heart data to indicate fetal distress, in indicating high-risk infants susceptible to sudden infant death syndrome (SIDS) by monitoring the heart-rate data of the infant, as a marker of aging, and in indicating risk for adverse cardiac events following surgery. Furthermore, the approximate entropy measure can be used to determine subtle arrhythmias that are not otherwise detectable.

TABLE 1a

TABLE OF RESULTS (HEALTHY)

| HEALTH | ApEn | VAR | WT(GMS.) | AGE(WKS) | SEX |
|---|---|---|---|---|---|
| 1. HEALTHY | 0.94 | 5.57 | 2050 | 36 | M |
| 2. HEALTHY | 1.08 | 6.99 | 1750 | 33 | F |
| 3. HEALTHY | 1.11 | 6.69 | 2010 | 31 | M |
| 4. HEALTHY | 1.12 | 10.29 | 1890 | 33 | F |
| 5. HEALTHY | 1.16 | 8.13 | 1800 | 34 | F |
| 6. HEALTHY | 1.20 | 9.42 | 550 | 24 | F |
| 7. HEALTHY | 1.24 | 8.53 | 1820 | 37 | F |
| 8. HEALTHY | 1.25 | 17.65 | 2020 | 41 | M |
| 9. HEALTHY | 1.27 | 8.56 | 3650 | 40 | M |
| 10. HEALTHY | 1.27 | 11.08 | 1300 | 34 | F |
| 11. HEALTHY | 1.29 | 11.95 | 1600 | 36 | F |
| 12. HEALTHY | 1.30 | 10.31 | 1730 | 33 | F |
| 13. HEALTHY | 1.30 | 9.54 | 3490 | 40 | F |
| 14. HEALTHY | 1.38 | 14.31 | 3100 | 40 | M |
| 15. HEALTHY | 1.40 | 15.10 | 4360 | 42 | M |

SUMMARY STATISTICS: (MEAN +/− SD)
ApEn: 1.22 +/− 0.12
VAR: 10.27 +/− 3.33
WT: 2210 +/− 1000
AGE: 35.6 +/− 4.7

TABLE 1b

TABLE OF RESULTS (SICK)

| HEALTH | ApEn | VAR | WT (GMS.) | AGE (WKS.) | SEX |
|---|---|---|---|---|---|
| 1. CONG.HF | 0.32 | 4.34 | 2430 | 34 | M |
| 2. PPH | 0.46 | 6.56 | 1090 | 27 | M |
| 3. PPH | 0.59 | 7.37 | 1090 | 27 | M |
| 4. CONG.HF | 0.69 | 10.49 | 3810 | 37 | F |
| 5. SEVERE RDS | 0.73 | 8.13 | 870 | 26 | M |
| 6. PPH | 1.02 | 11.70 | 1090 | 27 | M |
| 7. CONF.HF,DIAPH.HERN. | 1.03 | 7.88 | 2670 | 39 | M |
| 8. CONG. HF(TRI.18) | 1.15 | 11.61 | 2270 | 39 | F |
| 9. GI OBST.,TEF/Asp | 1.19 | 8.24 | 2640 | 40 | F |

SUMMARY STATISTICS: (MEAN +/− SD)
ApEn: 0.80 +/− 0.31
VAR: 8.48 +/− 2.42
WT: 2000 +/− 1010
AGE: 32.9 +/− 6.1
CONG. HF: CONGENITAL HEART FAILURE
DIAPH. HERN.: DIAPHRAGMATIC HERNIA
GI OBST.: GASTROINTESTINAL OBSTRUCTION
PPH: PERSISTENT PULMONARY HYPERTENSION
RDS: RESPIRATORY DISTRESS SYNDROME
TEF/Asp: TRACHEO-ESOPHAGEAL FISTULA WITH ASPIRATION
TRI.18: TRISOMY 18

Hormone Secretion Study

A study was performed to examine the potential applicability of ApEn to clinical endocrinology, and to quantify pulsatility in hormone secretion data. The study evaluated the role of ApEn as a complementary statistic to widely employed pulse detection algorithms, represented herein by ULTRA (Van Cauter, E., "Quantitative Methods for the Analysis of Circadian and Episodic Hormone Fluctuations," In *Human Pituitary Hormones: Circadian and Episodic Variations*, edited by E. Van Cauter and G. Copinschi, The Hague:Martinus Nyhoff, 1981:1–25), via the analysis of two different classes of models that generate episodic data. ApEn is able to discern subtle system changes and to provide insights separate from those given by ULTRA. ApEn evaluates subordinate as well as peak behavior, and often provides a direct measure of feedback between subsystems. ApEn generally can distinguish systems given 180 data points and an intraassay coefficient of variation of 8%. Additionally, the models and the extant clinical data are both consistent with episodic, not periodic, normative physiology. Thus, approximate entropy (ApEn), as a statistic, is applicable to hormone secretion data.

Given the presence of a non-trivial amount of noise, there are two steps in performing hormone secretion pulse analysis. The first is separating the "true" secretion time-series from the noise. The second step is in evaluating the resulting "true" time-series. While these two steps are typically commingled in each algorithm, this is a complementarity between ApEn and the pulse-identification algorithm, due to their different approaches to the second step. ApEn summarizes the time-series by a single number, whereas the pulse-identification algorithms identify peak occurrences and amplitudes. ApEn discerns changes in underlying episodic behavior that do not reflect in changes in peak occurrences or amplitudes, while the pulse-identification algorithms ignore such information.

Implicit to current models of hormone release is a periodicity assumption, with deviations attributed to noise. Two models which are capable of generating by themselves episodic, but not periodic, data are presented herein. In each model, there are several parameters that are varied, to generate a variety of data sets. For each model, ability of ApEn and a widely-used pulse-identification algorithm, ULTRA, to distinguish among the data sets generated by these models is evaluated. It is not suggested that these models represent known physiological systems, but rather these are offered as representative of alternative hypotheses to be considered when explaining observed episodic hormonal secretion. The present focus is not to propose a model that best mimics physiological reality, but rather to propose a new use of a statistic that gives different insights than are given by pulse-counting algorithms.

Episodic Hormone Secretion

Episodic, or pulsatile, secretion of hormones is an increasingly general finding in endocrinology. With the availability of sensitive radioimmunoassays (RIAs), which require only small sample volumes, protocols employing frequent sampling became possible. Furthermore, methods which help distinguish assay noise from biological variability make pulse detection a more rigorous endeavor. Studies employing such techniques in humans and diverse animal species have characterized pulsatile secretion of a large number of hormones, including luteinizing hormone (LH), insulin, progesterone, glucagon, growth hormone, ACTH, cortisol, prolactin, aldosterone, and HCG.

Elucidating the secretory patterns of hormone release has not only shed light on endocrine physiology, but also clarified the pathophysiology and improved the treatment of some diseases. For example, derangement in the episodic secretion of LH underlies some common disorders in humans, such as polycystic ovary syndrome, and hypogonadotropic hypogonadism. Administration of LHRH in a periodic fashion, designed to produce a normal LH secretory pattern, improved the pharmacologic therapy of these disorders. Similarly, elucidation of pulsatile insulin secretion in normal subjects laid the groundwork for the discovery of abnormal insulin secretory patterns on diabetic, and improved the efficacy of insulin replacement therapy by administration of the hormone in a periodic fashion.

Current Pulse-Identification Algorithms

The tools currently employed by endocrinologists to analyze the pulsatility of hormone secretion data fall under the aegis of peak-identification algorithms. The philosophy of these methods is to identify the "true" peaks in the data, distinct from apparent peaks generated by the random variations due to assay imprecision. Once these true peaks are identified, one may be able to determine normal and abnormal ranges of pulse frequency, amplitude, and duration, and hence potentially identify abnormal secretion. There are considerable differences among the algorithms, due to a variety of approaches in handling the intraassay noise. This intraassay variation typically has a coefficient of variation (CV) of between 6% and 14% (e.g., Fuchs, A. R., K. Goeschen, and P. Husslein, "Oxytocin and the Initiation of Human Parturition III: Plasma Concentration of Oxytocin and 13, 14-dihydro-15 Keto-prosaglandin F2-alpha in Spontaneous and Oxytocin-Induced Labor at Term," *Am. J. Obstet. Gynecol.* 147 (1983):497–502), an amount of noise that can in some instances make true peak detection very difficult. Nonetheless, for all of these algorithms, in the absence of noise, (i) one achieves identical peak detection, and (ii) changes in subordinate patterns that do not result in new or altered peaks are ignored.

The following eight pulse-detection programs are among those most widely available and extensively employed: Santen and Bardin (Santen, R. J., and C. W. Bardin, "Episodic Luteinizing Hormone Secretion in Man: Pulse Analysis, Clinical Interpretation, Physiologic Mechanisms," *J. Clin. Invest.* 52 (1973):2617–2628); modified Santen and Bardin; ULTRA; PULSAR (Merriam, G. R., and K. W. Wachter, "Algorithms for the Study of Episodic Hormone Secretion," *Am. J. Physiol.* 243 (1982):E310–318); Cycle Detector (Clifton, D. K., and R. A. Steiner, "Cycle Detection: A Technique for Estimating the Frequency and Amplitude of Episodic Fluctuations in Blood Hormone and Substrate Concentrations," *Endocrinology* 112 (1983): 1057–1064), Regional Dual Threshold (Veldhuis, J. D., J. Weiss, N. Mauras, A. D. Rogol, W. S. Evans, and M. L. Johnson, "Appraising Endocrine Pulse Signals at Low Circulating Hormone Concentrations: Use of Regional Coefficients of Variation in the Experimental Series to Analyze Pulsatile Luteinizing Hormone Release. *Pediatr. Res.* 20 (1986):632–637), Cluster (Veldhuis, J. D., and M. L. Johnson, "Cluster Analysis: A Simple, Versatile, and Robust Algorithm for Endocrine Pulse Detection," *Am. J. Physiol.* 250 (1986):E486–493); and Detect (Oerter, K. E., V. Guardabasso, and D. Rodbard, "Detection and Characterization of Peaks and Estimation of Instantaneous Secretory Rate for Episodic Pulsatile Hormone Secretion," *Comput. Biomed. Res.* 19 (1986):170–191). The similarity of the pulse-identification algorithms in the presence of negligible noise, the apparent relative robustness to non-trivial CVs, the usefulness with 50 to 200 data points, and the philosophy of peak analysis as the means to evaluate pulsatility bond this class of algorithms together. ULTRA has been chosen as representative of these algorithms in performing the comparisons with ApEn below. It is expected that another choice of pulse-detection algorithm, for the purpose of comparison with ApEn, would give quite similar results.

Based on published time-series of hormonal concentration levels, there is the need for an added dimension in the analysis of episodic hormone release, beyond monitoring the pulse count and related statistics. Lang et al., (Lang, D. A., D. R. Matthews, and R. C. Turner, "Brief, Irregular Oscillations of Basal Plasma Insulin and Glucose Concentrations in Diabetic Men," *Diabetes* 30 (1981):435–439) conclude that brief, irregular oscillations in plasma insulin levels, in maturity-onset diabetics, are superimposed on longer term oscillatory fluctuations commonly observed in the non-diabetic. ApEn provides a quantification of the regularity of these data, which is useful for distinguishing a diabetic's insulin secretion patterns from those of a non-diabetic.

Furthermore, episodic variation in hormones often has revealed complex patterns, challenging existing programs to characterize, and then differentiate, a "diseased" pattern from a healthy one. Finally, frequency distributions of discrete LH pulse properties, given by Urban (Urban, R. J., W. S. Evans, A. D. Rogol, D. L. Kaiser, M. L. Johnson, and J. D. Veldhuis, "Contemporary Aspects of Discrete Peak-Detection Algorithms: I. The paradigm of the Luteinizing Hormone Pulse Signal in Men," *Endocrine Revs.* 9 (1988) :3–37) and based on nearly 200 pulses, show significantly non-Gaussian distributions for both pulse frequencies and amplitudes. The asymmetry of these distribution is not consonant with the typical assumption of periodic pulses in the presence of symmetrically distributed noise. One thus either concludes a lack of periodicity in these LH pulses, or at least must entertain the possibility of such a periodicity in constructing algorithms to analyze such series.

The crucial difficulty in applying conventional entropy measurements to hormone secretion data is that hormone secretion data are relatively few in number (at most, several hundred data points), whereas an accurate conventional entropy calculation for an underlying system of dimension d typically requires from $10^d$ to $30^d$ data points (Wolf, A., J. B. Swift, H. L. Swinney, and J. A. Vastano, "Determining Lyapunov Exponents from a Time-Series," *Physica* 16D (1985):285–317). The number of data points is key, because there is no reason to anticipate, and no evidence to show, that data typically encountered from such complex interacting systems of glands and hormones that form endocrine systems be low-dimensional. Furthermore, one cannot assume that hormonal secretion is correctly modelled by deterministic chaos, as opposed to a stochastic model.

ApEn has many of the characteristics deemed important for effective characterization of episodic hormone release as described by Urban et al. ApEn is objective, simple to use, via existing FORTRAN and C-language computer programs, and ApEn produces a single number. ApEn has minimal dependence on the specific type of signal or noise present in the underlying data. ApEn is versatile; it can be used for any time-series data analysis, to compute a measure of regularity. For hormone pulse detection, ApEn is readily adaptable to differences in sampling frequency and duration, assay performance, and signal-noise ratios. ApEn is very stable to small changes in noise characteristics, infrequent and significant data artifacts, and changes in sampling frequency. ApEn is concordant with visual inspection. ApEn accounts for a variety of dominant and subordinate patterns in data; notably, ApEn is affected by changes in underlying episodic behavior that do not reflect in changes in peak occurrences or amplitudes.

Additionally, ApEn provides a direct barometer of feedback system change in some coupled systems. Thus, ApEn is useful in shedding insight into interactions among hormones, indicating a source of underlying physiologic deviations, such as a breakdown in the normal system feedback process.

Model Comparison Framework

Results from ApEn and ULTRA calculations for test data from two models are discussed below. To calculate ApEn and ULTRA for these data, certain inputs in each algorithm must be specified. For ApEn, m is set to 2 throughout the models, and r is chosen, fixed for each model, to equal about 20% of the standard deviation of a typical data set. This results in choices of r=0.4 for the Ueda model and r=0.1 for the Rossler model, consistent with guidelines given by Pincus (Pincus, S. M., I. M. Gladstone, and R. A. Ehrenkranz, "A Regularity Statistic for Medical Data Analysis," *J. Clin. Monit.* 7(4) (October 1991):335–345)

For ULTRA, 3 CVs are chosen as the threshold for the Ueda model, and 2 CVs are chosen as the threshold for the Rossler model. This is consistent with Van Cauter's guidelines (applied to the "predominant" pattern in each instance). To determine concentration ranges and CV values for each range, one works backwards from the noise standard deviation data given in each version of each model. In each version, there is a model in which Gaussian noise of a fixed standard deviation (sdev) is superimposed on all the data, to model the inaccuracy of assay measurements. The output concentration ranges, for each time series, is divided into 8 pieces, each with a mean m. For each range, the CV is set to be sdev/m.

The output of ApEn is a number, while the output of ULTRA is an identified set of peaks of pulses in the data. From each ULTRA output, the number of pulses, the average and standard deviation of pulse lengths, and the average and standard deviation of pulse amplitudes are calculated. For each model, a table is used to summarize the runs. Each line in the tables lists the run number, number of data points in the time series, and input model characteristics: parameter choices, and standard deviation of superimposed Gaussian noise. The output data includes the mean and standard deviation of the time series, ApEn value, number of pulses, and mean and standard deviation for both pulse frequency and pulse amplitude.

Ueda Differential Equation Model

Figure 7A:
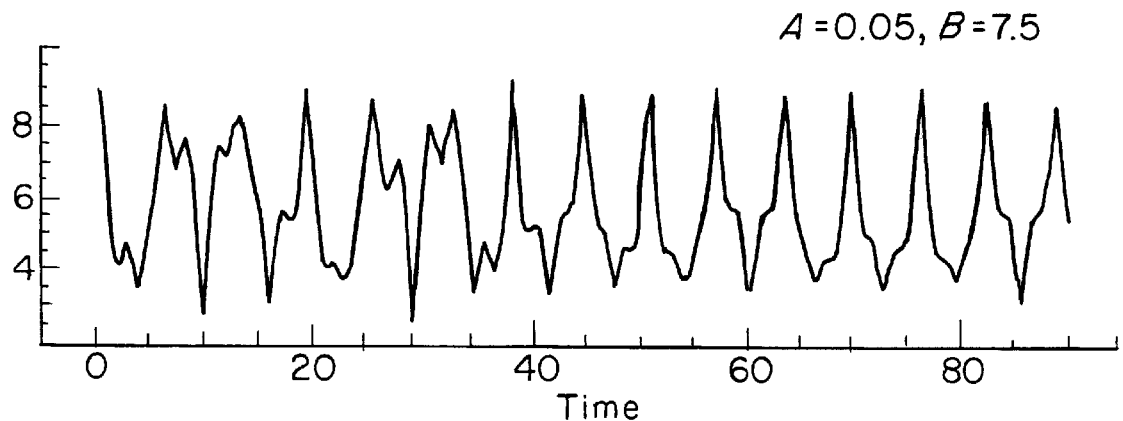
FIGS. 7A–C are Ueda differential equation model time-series output for three pairs of parameter values.
Figure 7B:
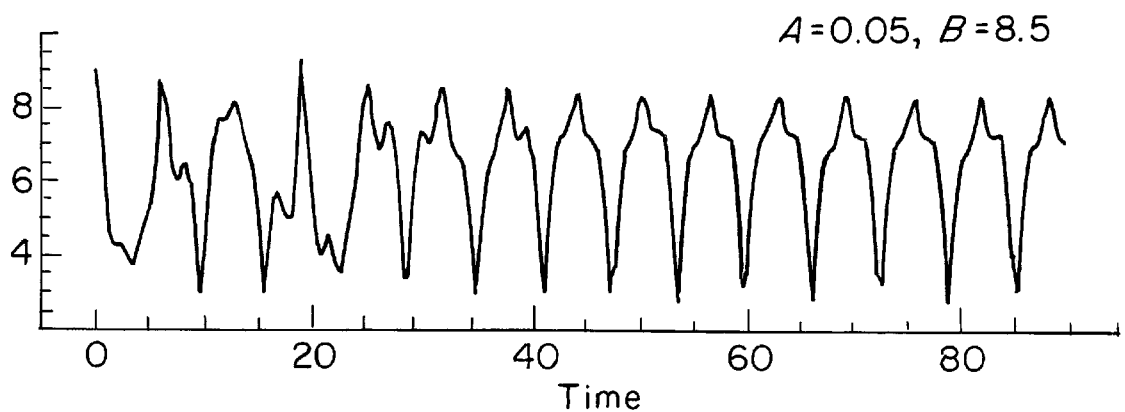
Figure 7C:
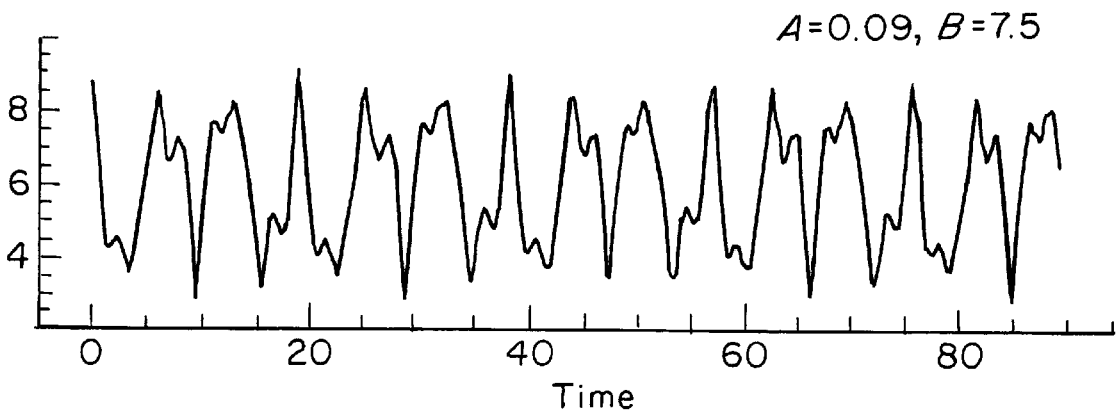

The equation $$\ddot{x}+A\dot{x}+x^3=B\cos t \quad (5)$$

is a differential equation that has received considerable attention in recent years, due in great part to studies by Ueda (Ueda, Y., "Steady Motions Exhibited by Duffing's Equation: A Picture Book of Regular and Chaotic Motions," *In New Approaches to Nonlinear Problems in Dynamics*, edited by P. J. Holmes, Philadelphia, PA.:SIAM, 1980:311–322) showing that the long-term dynamics of the solution represent steady-state chaotic behavior, for parameter values A=0.05, B=7.5. This equation, where the dots denote differentiation with respect to time t, describes the behavior of the variable x over time; for each time, the corresponding value of x can be calculated (via numerical methods), to deduce a time-plot of x as illustrated in FIGS. 7A–C. Equation 5 may be used in mechanical engineering, e.g., to model the motion of a sinusoidally forced structure undergoing large elastic deflections. The solution is bounded, episodic, yet nonperiodic.

Here, Equation 5 is analyzed for five (A,B) pairs: (0.05, 7.5), (0.05, 8.5), (0.05, 12.0), (0.09, 7.5), and (0.21, 7.5). For each pair, equation 5 is solved as a function in time by an explicit time step method, Δt=0.002. A time series is extracted from the solution by sampling every 0.5 t-units. This sampling rate was chosen to yield about 12 data points per episode, and generates the baseline series. This is consistent with Yates, (Yates, F. E., "Analysis of Endocrine Signals: The Engineering and Physics of Biochemical Communication Systems", Bio. Reprod. 24 (1981):73–94), where samples of at least 6 times the expected frequency are seen as necessary to deduce periodicities, and with Veldhuis (Veldhuis, J. D., W. S. Evans, A. D. Rogol, C. R. Drake, M. O. Thorner, G. R. Merriam, and M. L. Johnson, "Intensified Rates of Venous Sampling Unmask the Presence of Spontaneous, High Frequency Pulsation of LH in Men," J. Clin. Endocrinol. Metab. 59 (1984):96–102), which notes the clinical need for intensified sampling rates. The solution time-series is post-processed by converting x to x+6.0 for all data values. This is done to ensure positive values, in the range 3.0 to 9.0, to mimic endocrine data. Uniform white noise is added to each baseline value to deduce the final series. For each pair, two different lengths of series are analyzed, 180 points and 900 points. For (0.05, 7.5) and (0.05, 8.5), the series is analyzed with 2000 points.

This model is analyzed for two primary reasons. First, the model exemplifies a simple system which gives rise to highly nontrivial, putatively pulsatile behavior. Second, the model forces a careful examination of the meaning of pulsatility, to ensure that the quantitative tools used reasonably correspond to intuitive expectations. The crucial property of the solution to the Ueda equation is that it is episodic, but truly non-periodic. The equation's recurrent nature is evidenced by the fact that certain patterns in the waveform repeat themselves at irregular intervals, but there is never exact repetition. There is an apparent baseline frequency per episode (pulses), though there is temporal variation of a non-periodic nature. Furthermore, there are second-order, irregularly varying wiggles in the episodes that are generated by the model itself.

This system is an appropriate model for hormone secretion, with normal secretion given by a model with A and B as stated above fixed, with A=0.5, and B between 8.5 and 12.0. On the basis of time-series data alone, the system can detect that certain data came from an "abnormal" system for which A=0.5 and B=15.0.

As reported by Table 2, runs 1–10, the pulse count for noiseless systems is given as half the number of sign changes. This property is common to many of the current pulse identification algorithms, in which a pulse is flagged as a measured rise and fall, with both the rise and fall indicated by some percentage rise and fall times the noise level.

TABLE 2

| Run No | No. of Points | Ueda Parameters K | B | Input Noise SD | Mean | SD | ApEn | No. of Sign Changes | No. of Pulses | Avg. Freq. | SD Freq. | Avg. Amp | SD Amp |
|---|---|---|---|---|---|---|---|---|---|---|---|---|---|
| 1 | 180 | 0.05 | 7.5 | 0.0 | 5.808 | 1.593 | 0.677 | 56 | 28 | 6.185 | 2.450 | 7.368 | 1.834 |
| 2 | 180 | 0.05 | 8.5 | 0.0 | 6.401 | 1.612 | 0.543 | 50 | 25 | 6.792 | 3.400 | 7.771 | 1.276 |
| 3 | 180 | 0.09 | 7.5 | 0.0 | 6.074 | 1.650 | 0.574 | 66 | 33 | 5.406 | 1.292 | 7.363 | 1.596 |
| 4 | 180 | 0.05 | 12.0 | 0.0 | 5.992 | 1.781 | 0.762 | 81 | 40 | 4.410 | 1.044 | 7.406 | 1.692 |
| 5 | 180 | 0.21 | 7.5 | 0.0 | 6.174 | 1.549 | 0.676 | 46 | 23 | 7.818 | 3.390 | 7.624 | 1.338 |
| 6 | 900 | 0.05 | 7.5 | 0.0 | 5.973 | 1.597 | 0.894 | 275 | 137 | 6.463 | 2.839 | 7.476 | 1.576 |
| 7 | 900 | 0.05 | 8.5 | 0.0 | 6.533 | 1.567 | 0.466 | 213 | 105 | 8.452 | 4.031 | 8.028 | 0.769 |
| 8 | 900 | 0.09 | 7.5 | 0.0 | 6.034 | 1.637 | 0.590 | 333 | 166 | 5.388 | 1.447 | 7.335 | 1.570 |
| 9 | 900 | 0.05 | 12.0 | 0.0 | 6.068 | 1.758 | 1.153 | 401 | 200 | 4.462 | 1.131 | 7.531 | 1.540 |
| 10 | 900 | 0.21 | 7.5 | 0.0 | 5.908 | 1.550 | 0.666 | 227 | 112 | 7.991 | 3.361 | 7.635 | 1.550 |
| 11 | 900 | 0.05 | 7.5 | 0.05 | 5.971 | 1.597 | 0.904 | 281 | 117 | 7.578 | 3.492 | 7.731 | 1.486 |
| 12 | 900 | 0.05 | 7.5 | 0.1 | 5.968 | 1.599 | 0.953 | 287 | 104 | 8.534 | 3.694 | 7.925 | 1.393 |
| 13 | 900 | 0.05 | 7.5 | 0.2 | 5.963 | 1.609 | 1.091 | 299 | 97 | 9.156 | 3.675 | 8.098 | 1.250 |
| 14 | 900 | 0.05 | 7.5 | 0.4 | 5.953 | 1.647 | 1.336 | 367 | 84 | 10.59 | 3.425 | 8.417 | 0.975 |
| 15 | 900 | 0.05 | 8.5 | 0.05 | 6.530 | 1.567 | 0.473 | 213 | 77 | 11.57 | 2.568 | 8.311 | 0.611 |
| 16 | 900 | 0.05 | 8.5 | 0.1 | 6.528 | 1.569 | 0.510 | 253 | 76 | 11.72 | 2.408 | 8.320 | 0.603 |
| 17 | 900 | 0.05 | 8.5 | 0.2 | 6.523 | 1.577 | 0.742 | 289 | 78 | 11.41 | 2.769 | 8.305 | 0.613 |
| 18 | 900 | 0.05 | 8.5 | 0.4 | 6.513 | 1.614 | 1.196 | 379 | 77 | 11.57 | 2.806 | 8.479 | 0.400 |
| 19 | 900 | 0.09 | 7.5 | 0.05 | 6.031 | 1.638 | 0.602 | 333 | 165 | 5.421 | 1.486 | 7.332 | 1.575 |
| 20 | 900 | 0.09 | 7.5 | 0.1 | 6.029 | 1.640 | 0.634 | 335 | 155 | 5.773 | 1.881 | 7.371 | 1.582 |
| 21 | 900 | 0.09 | 7.5 | 0.2 | 6.024 | 1.650 | 0.909 | 339 | 121 | 7.408 | 3.245 | 7.789 | 1.390 |
| 22 | 900 | 0.09 | 7.5 | 0.4 | 6.014 | 1.687 | 1.292 | 365 | 92 | 9.769 | 3.715 | 8.340 | 1.029 |
| 23 | 2,000 | 0.05 | 7.5 | 0.0 | 6.075 | 1.597 | 0.871 | 588 | 294 | 6.782 | 3.116 | 7.544 | 1.469 |
| 24 | 2,000 | 0.05 | 8.5 | 0.0 | 6.559 | 1.556 | 0.443 | 460 | 229 | 8.715 | 4.077 | 8.069 | 0.639 |

In the absence of noise, any rise is considered a pulse ascent, and any fall considered a pulse descent. Therefore, to evaluate ULTRA as a pulse-counting algorithm, it suffices to examine the statistical properties of the algorithm that counts the number of sign changes. This statistic has been extensively examined (Sen, P. K., "Signed-Rank Statistics," In Encyclopedia of Statistical Sciences 8, edited by S. Kotz and N. L. Johnson. New York:John Wiley, 1988:461–466) and provides useful information. It does not, however, utilize any information contained in the magnitudes associated with the sign changes, so that a tiny wiggle counts as much as a large wave. An instance of an improved measure is given by the Wilcoxon signed-rank statistic, a standard non-parametric statistical test. In this context, ranks would be given to the sign changes, with the largest rank to the greatest sign change. Hence, big pulses "count" more than little pulses, possibly a desired characteristic in the goal to distinguish normal from abnormal behavior.

A central issue for this model is apparent upon examination of FIGS. 7A–C. Time-series output is shown in FIGS. 7A–C for three pairs of parameter values, (a) K=0.05, B=7.5, (b) K=0.05, B=8.5, and (c) K=0.09, B=7.5, respectively. These series are apparently different, but quantitative tools to distinguish them are not a priori apparent. These series have mean approximately equal to 6, standard deviation approximately equal to 1.6. Each series has a "period" of 2π, but no two periods are identical; there are different peak amplitudes, shapes, and subordinate "wiggles" throughout. Both ApEn and ULTRA distinguish versions of this model, but the results require scrutiny, because they appear to be in disagreement.

First, runs 1–10, are summarized in Table 2. They represent runs for the five K-B pairs specified above, for two series lengths, 180 points and 900 points. According to ApEn, these versions rank (from most random to least random, in descending order) as (0.05, 12.0), (0.05, 7.5), (0.21, 7.5), (0.09, 7.5), (0.05, 8.5). This order is maintained for both 180 and 900 points, although several distinctions are sharper for 900 points than for 180 points. For this model, 900 points yields good convergence for ApEn; comparing run 6 to run 23 (900 vs. 2000 points, K=0.05, B=7.5), ApEn changes from 0.894 to 0.871. Similarly, comparing run 7 to run 24, (900 vs. 2000 points, K=0.05, B=8.5), ApEn changes from 0.466 to 0.443.

According to ULTRA, these versions rank (from most random to least random) as (0.05, 12.0), (0.09, 7.5), (0.05, 7.5), (0.21, 7.5), (0.05, 8.5). This order is nearly maintained for both 180 and 900 points, although the last two versions reverse order in the 180 and 900 point cases. Furthermore, with the exception of the (0.05, 8.5) case, a five-fold increase in point count corresponds to virtually a five-fold increase in pulse number. This ratio of pulses to points is maintained in the two 2000-point runs, hence the 900-point runs are sufficiently long to extract the salient pulse information here. However, there is an apparent conflict over which of (0.05, 7.5) or (0.09, 7.5) is more random (unpatterned).

The Poincare section is a tool to resolve this impasse. First, a phase space plot is generated (for each series), plotting the trajectory of x versus its time derivative, dx/dt. To insure a sequence of strictly comparable points, the trajectory is marked stroboscopically at times that are an integer multiple of the forcing period 2π. The resulting plot, in the x–dx/dt plane, shows only the strobed points as the Poincare section. If the motion of the system were strictly periodic with the frequency of the forcing, the strobe point would all be the same point, repeating indefinitely. If the true motion were multiply periodic, then a sequence of n dots would appear, repeated indefinitely. More complicated dynamics are represented by more filled out Poincare section portraits, which correspond to greater ApEn.

It can be shown (data not shown) that FIG. 7A has the most complicated dynamics, FIG. 7C has the next most complicated dynamics, and FIG. 7B has the least complicated dynamics. This corresponds to a greatest randomness for (0.05, 7.5), then (0.09, 7.5), followed by (0.05, 8.5), the order given by ApEn. Furthermore, the respective ApEn values, 0.894, 0.590, and 0.466, seem to correspond to the intuition that the (0.09, 7.5) case is closer to the (0.05, 8.5) case in randomness than to the (0.05, 7.5) case.

The apparent inconsistency in ULTRA is explained by its equal weighting of each of many tiny wiggles and the larger sign changes. The (0.09, 7.5) case has the greatest number of sign changes of the three cases examined in FIGS. 7A–C, but these sign changes, particularly the "small wiggles," tend to occur near similar locations in each major "pulse." This can be virtually expressed by areas of darker clustering in phase portraits. Greater randomness would be marked by a greater spread of these dark clusters. The last point reemphasizes the foibles of the sign change algorithm, as opposed to a weighted sign change algorithm.

Returning to Table 2, runs 11–22 further illustrate the difficulties that these small wiggles pose for ULTRA. For each of the versions (0.05, 7.5), (0.05, 8.5), and (0.9, 7.5), four different noise levels, standard deviations of 0.05, 0.1, 0.2, and 0.4, corresponding to CVs of approximately 1%, 2%, 4%, and 8%. In the (0.05, 7.5) case, ULTRA noted 137 pulses at 0 noise, compared to 117 pulses at 0.05 noise, and 104 pulses at 0.1 noise. This represents a computational loss of about 15% of pulses at 1% CV. In the (0.05, 8.5) case, ULTRA noted 105 pulses at 0 noise, compared to roughly 77 pulses in the presence of at least 0.05 noise. These 77 pulses represent, almost solely, the large pulses of approximate duration 2π. Virtually all the small wiggles were effectively ignored in the presence of the noise levels noted above. This represents a computational loss of about 27% of pulses at 1% CV. In the (0.09, 7.5) case, ULTRA behaved more robustly at low noise levels, with 166 pulses at 0 noise, 165 pulses at 0.05 noise, and 155 pulses at 0.1 noise.

ApEn performs more robustly at low noise levels. In the (0.05, 7.5) case, ApEn is 0.894 at 0 noise, 0.904 at 0.05 noise, and 0.953 at 0.1 noise. In the (0.05, 8.5) case, ApEn is 0.466 at 0 noise, 0.473 at 0.05 noise, and 0.510 at 0.1 noise. In the (0.09, 7.5) case, ApEn is 0.590 at 0 noise, 0.602 at 0.05 noise, and 0.634 at 0.1 noise. These all represent about a 1% to 2% change at 1% CV, and a 7% to 9% change at 2% CV.

Figure 8A:
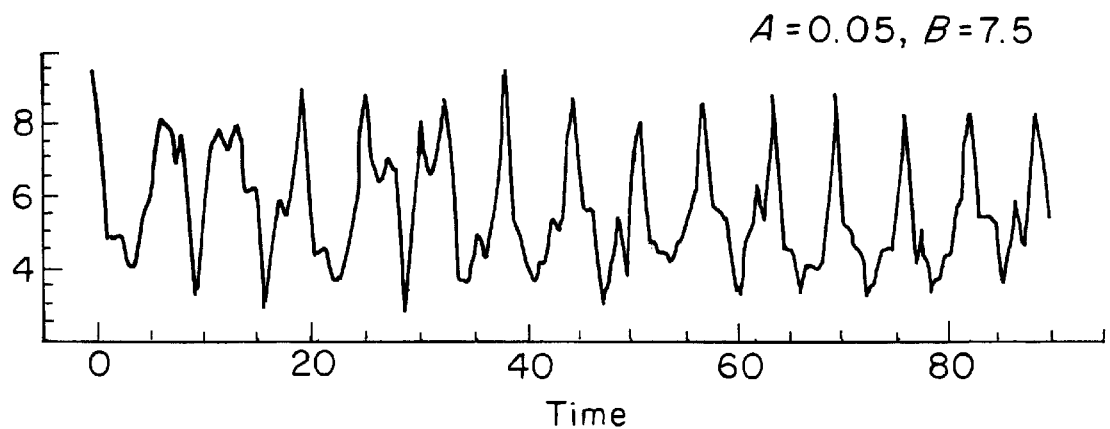
FIGS. 8A–C are Ueda differential equation model time-series output with Gaussian noise superimposed for the parameter values of FIGS. 7A–C.
Figure 8B:
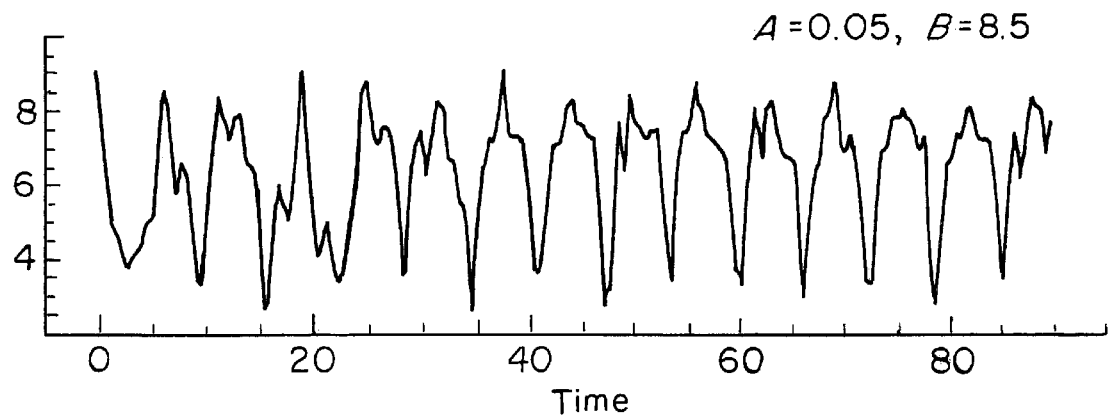
Figure 8C:
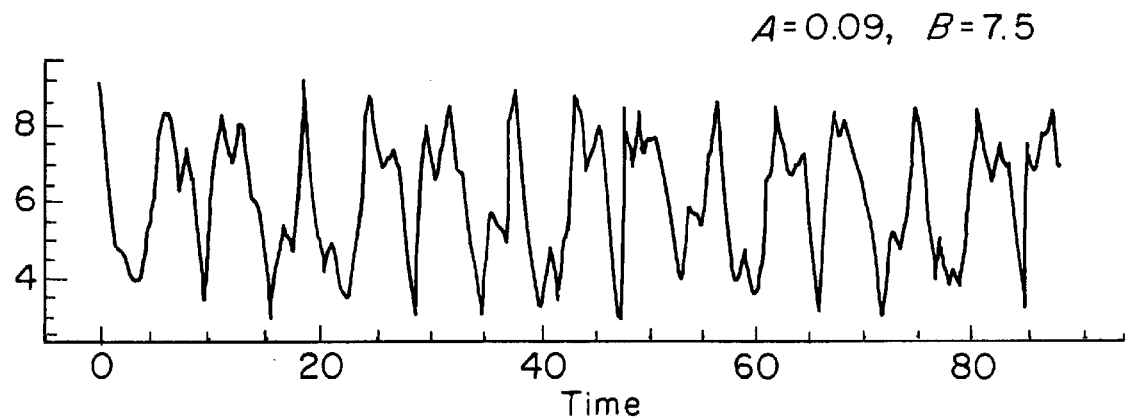
Figure 9A:
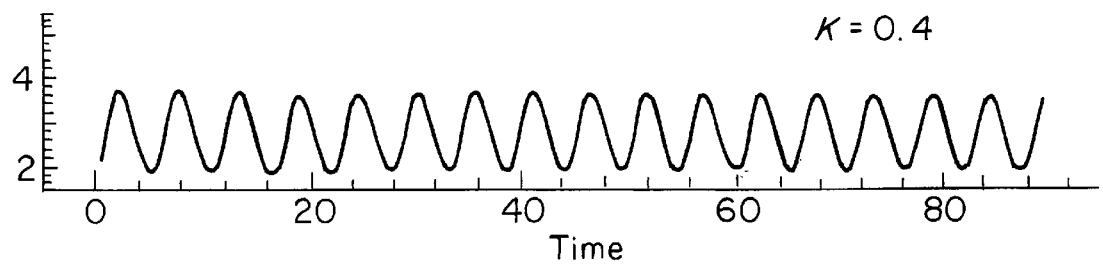
FIGS. 9A–E illustrate luteinizing hormone (LH) time-series output for five coupling parameters in the Rossler coupled differential equation model.
Figure 9B:
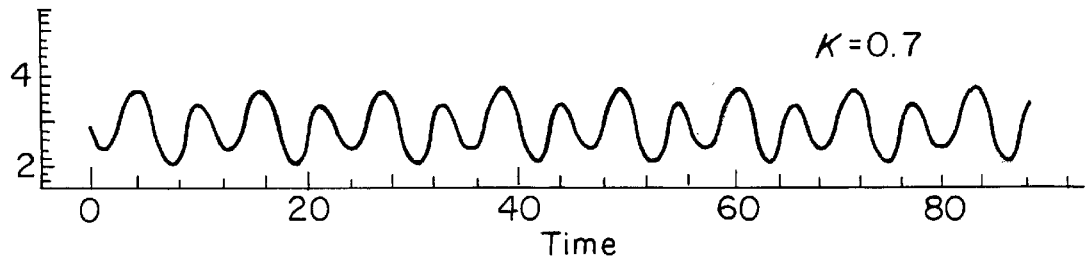
Figure 9C:
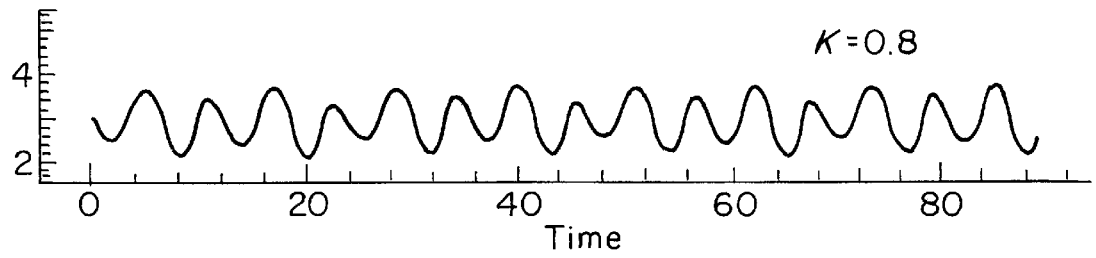
Figure 9D:
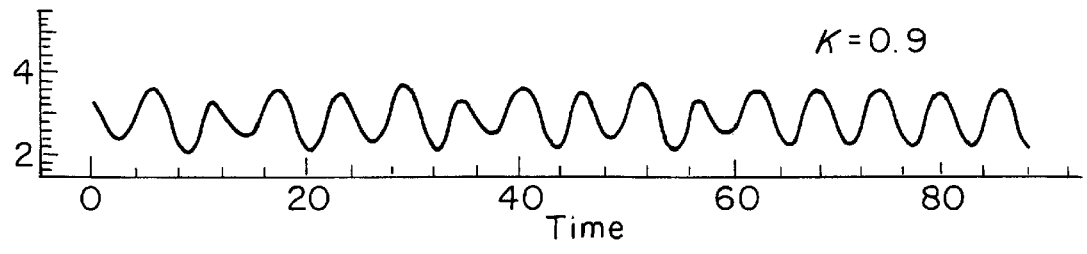
Figure 9E:
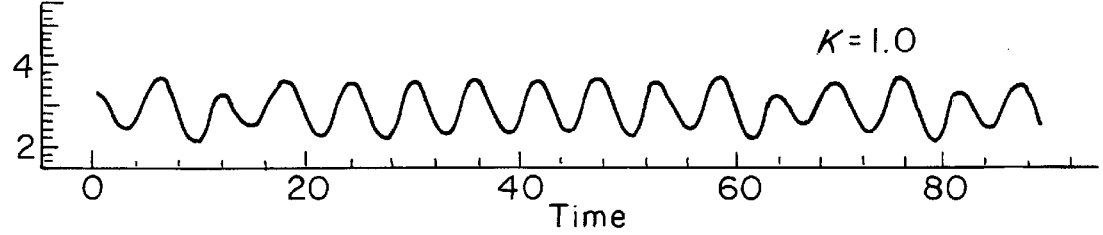

At each noise level ApEn maintains the order of randomness of these versions, although system distinction is much less marked at 0.4 noise level, as shown in FIGS. 8A–C, at which ApEn values are 1.336 for the (0.05, 7.5) case, 1.196 for the (0.05, 8.5) case, and 1.292 for the (0.09, 7.5) case. ULTRA also maintains its order of ranking these versions, with pulse counts of 84, 77, and 92 in the same three cases at 0.4 noise standard deviation. It is not surprising that the distinctions among the versions are muddied at this noise level; some of the small wiggles in the base physiological cases are accentuated, some are eliminated, and some new small wiggles emerge with 0.4 level noise.

From analysis of this model, in the presence of noise, ULTRA tends to smooth out the time-series data, in effect eliminating some small wiggles in the process. In some contexts, that may be desirable, but in instances such as this model, in which numerous small, subordinate pulses are present, ULTRA is discarding physiological information.

Rossler Feedback Model

The Rossler Feedback Model is a coupled system of three variables, represented by three ordinary differential equations. This is considered as a putative model for the male reproductive endocrine system, with variables the pituitary portal concentration of LHRH, and the serum concentrations of luteinizing hormone (LH) and testosterone (T). These concentrations are modelled by a coupled feedback system: the LHRH secretion rate is given as a function of the local concentrations of LH and serum testosterone. The LH secretion rate is given as a function of the concentration of LHRH, plus a rate proportional to its own concentration. The testosterone secretion rate is given as a rate proportional to its own concentration, plus a term proportional to the product of the LHRH and testosterone levels. This feedback system is represented as follows, with K to be specified:

$$\dot{LHRH} = -(LH + T) \quad (6)$$
$$\dot{LH} = LHRH + 0.2 LH$$
$$\dot{T} = 0.2 + K(LHRH^*T - 5T)$$

For each time, and each value of K, the corresponding concentration levels are calculated by an explicit time step method, Δt=0.005. A time series is extracted from the solution by sampling every 0.5 t-units. For suitable choices of K, the solutions have many of the qualitative features seen in clinical endocrine data. Here each version is defined by a choice for K. Changes in K can be thought to mirror the intensity of interaction between testosterone and LHRH levels.

This system is analyzed for coupling levels K=0.4, 0.7, 0.8, 0.9, and 1.0. All this is done in a post-transient setting, in which the first 90 t-units are omitted from consideration. The solution time-series is then "post-processed" as follows, to ensure positive values: convert LHRH to 0.1(LHRH)+3.0, convert LH to 0.1(LH)+3.0, and T to 0.1(T)+3.0. Add white noise to each baseline value, for each of LHRH, LH, and T to deduce the time-series solution to the coupled system. For each noiseless version, two different lengths of series, 180 points and 900 points are analyzed. For the 900 point series, analyze three different versions of the model, K=0.7, 0.8, and 0.9, each under four different noise levels, noise standard deviations of 0.02, 0.05, 0.1, and 0.2. For K=0.8 and K=1.0, also analyze the series with 2000 points.

This model is similar to one examined by Rossler (Rossler, O. E., "An Equation for Continuous Chaos," *Phys. Lett.* 57A (1976):397–398) as an example of a system that produced chaotic behavior for certain parameter values of K. It is also thematically similar to models by Smith, which are meant to plausibly model the male endocrine system, and are shown to capture some of the essential physiological dynamics of the true reproductive system. The Rossler model was analyzed, rather than the Smith model, for pedagogic reasons: distinctions among versions are sharper for the Rossler model than for the Smith model, though qualitatively quite similar. In any case, this model was analyzed for some of the reasons given by Smith. Relatively simple versions of this system can explain a number of possible qualitative modes of hormonal dynamics: serum concentrations that are constant in time, periodic in time, or chaotic in time. Most importantly, different behavioral modes can result solely from changes in defining system parameters, or internal interactions among the system subcomponents, and need not be produced by and external, driving force. For example, the onset of puberty, in one version of Smith's model, is seen to be generated simply by an appropriate change in certain system parameters, without an external switch or component entering into the fray.

Furthermore, the Rossler model is substantially different from the Ueda model. In particular, the Rossler model is a function of several variables, and is an explicit feedback system. Thus, it is possible that neither ApEn nor ULTRA may detect changes in the feedback (coupling) rate, as seen by varying K. The model analyzed here was chosen to give either periodic, multiply periodic, or chaotic output for the behavior of LH with time, depending on K. In general, with increasing K, there is increasing system complexity: the LH behavior evolves from periodic to multiply periodic to chaotic.

FIGS. 9A–E illustrate LH time-series output for the five coupling parameters of the Rossler coupled differential equation model, K=0.4, 0.7, 0.8, 0.9, and 1.0 in a noiseless environment. Virtually an identical pulse count is apparent in each of these systems. For K=0.4, the system is strictly periodic, while for K=0.7, the system is "twice-periodic," with a higher pulse always followed by a smaller pulse. The system is "four-times periodic" for K=0.8 (high-low-highest-lowest), and chaotic for K=0.9, and K=1.0. In these last two instances, no pattern of multiple pulses forms a fundamental period of its own.

The increase in system complexity with increasing K can be further confirmed by phase-space plots. Phase- space plots serve a similar purpose to Poincare sections, to geometrically capture complexity via an appropriate perspective on the data. In a phase-space plot, the trajectory of LHRH versus LH is plotted so each point represents a single "LHRH-LH" pair of values at a fixed instant. Increased complexity manifests itself in more complicated phase-space portraits, which here is with increasing K. If the motion of the LH-system were singly periodic, the portrait would be a simple closed curve. Multiple periodicity is shown by multiple loops in a closed curve. Chaotic behavior is not represented by closed curves. Fine system structure in these versions is apparent with phase- space portraits produced from much longer time-series input than considered here.

ULTRA's evaluation of the respective noiseless model versions is considered in runs 1–10 of Table 3. Runs 1–5 and 6–10 are 180 and 900 points long, respectively, with each set of 5 runs arranged in increasing K. Runs 1–5 give either 15 or 16 pulses for each series, and runs 6–10 give between 77 and 82 pulses for each series, indicating little version distinction based on pulse count. For the other statistics there is a distinct difference between the K=0.4 case and the other four versions, all of which produce quite similar values. In runs 7–10, the average frequency ranges from 11.28 to 11.63, the standard deviation of the frequency ranges from 0.636 to 0.650, the average amplitude ranges from 3.50 to 3.56, and the standard deviation of the amplitude ranges from 0.130 to 0.175. Only the last of these statistics, the amplitude standard deviation, shows any spread among the four versions, and even for this statistic, the lowest value is achieved for K=0.9, with both K=0.8 and K=1.0 versions slightly higher. This conflicts with intuition, which suggests that a lowest value for each of these statistics should be for either the least or the most complex system.

TABLE 3

| | | ULTRA Statistics | | | | | | | | | | |
|---|---|---|---|---|---|---|---|---|---|---|---|---|
| Run No | No. of Points | Coupling Parameters K | Input Noise SD | Mean | SD | ApEn | No. of Sign Changes | No. of Pulses | Avg. Freq. | SD Freq. | Avg. Amp | SD Amp |
| 1 | 180 | 0.4 | 0.0 | 2.774 | 0.692 | 0.165 | 32 | 16 | 10.93 | 0.258 | 3.764 | 0.015 |
| 2 | 180 | 0.7 | 0.0 | 2.871 | 0.529 | 0.266 | 32 | 15 | 11.26 | 0.775 | 3.540 | 0.227 |
| 3 | 180 | 0.8 | 0.0 | 2.882 | 0.499 | 0.442 | 31 | 15 | 11.29 | 0.727 | 3.512 | 0.187 |
| 4 | 180 | 0.9 | 0.0 | 2.902 | 0.476 | 0.472 | 30 | 15 | 11.50 | 0.650 | 3.513 | 0.142 |
| 5 | 180 | 1.0 | 0.0 | 2.918 | 0.453 | 0.489 | 30 | 15 | 11.64 | 0.497 | 3.498 | 0.138 |
| 6 | 900 | 0.4 | 0.0 | 2.772 | 0.689 | 0.165 | 164 | 82 | 10.91 | 0.283 | 3.765 | 0.014 |
| 7 | 900 | 0.7 | 0.0 | 2.872 | 0.527 | 0.262 | 159 | 79 | 11.28 | 0.643 | 3.560 | 0.175 |
| 8 | 900 | 0.8 | 0.0 | 2.887 | 0.495 | 0.431 | 157 | 78 | 11.42 | 0.636 | 3.535 | 0.160 |
| 9 | 900 | 0.9 | 0.0 | 2.897 | 0.475 | 0.495 | 155 | 77 | 11.55 | 0.641 | 3.528 | 0.130 |

TABLE 3-continued

ULTRA Statistics

| Run No | No. of Points | Coupling Parameters K | Input Noise SD | Mean | SD | ApEn | No. of Sign Changes | No. of Pulses | Avg. Freq. | SD Freq. | Avg. Amp | SD Amp |
|---|---|---|---|---|---|---|---|---|---|---|---|---|
| 10 | 900 | 1.0 | 0.0 | 2.910 | 0.454 | 0.510 | 154 | 77 | 11.63 | 0.650 | 3.500 | 0.139 |
| 11 | 900 | 0.7 | 0.02 | 2.872 | 0.529 | 0.323 | 159 | 79 | 11.28 | 0.662 | 3.560 | 0.178 |
| 12 | 900 | 0.7 | 0.05 | 2.872 | 0.532 | 0.633 | 161 | 79 | 11.28 | 0.804 | 3.563 | 0.184 |
| 13 | 900 | 0.7 | 0.2 | 2.874 | 0.571 | 1.453 | 354 | 83 | 10.72 | 2.251 | 3.650 | 0.242 |
| 14 | 900 | 0.7 | 0.1 | 2.873 | 0.540 | 1.112 | 227 | 79 | 11.27 | 1.101 | 3.587 | 0.196 |
| 15 | 900 | 0.8 | 0.02 | 2.887 | 0.495 | 0.503 | 157 | 78 | 11.42 | 0.695 | 3.537 | 0.162 |
| 16 | 900 | 0.8 | 0.05 | 2.888 | 0.497 | 0.761 | 161 | 78 | 11.42 | 0.950 | 3.548 | 0.168 |
| 17 | 900 | 0.8 | 0.2 | 2.890 | 0.535 | 1.544 | 365 | 83 | 10.72 | 2.229 | 3.636 | 0.269 |
| 18 | 900 | 0.8 | 0.1 | 2.888 | 0.505 | 1.167 | 213 | 79 | 11.27 | 1.429 | 3.583 | 0.178 |
| 19 | 900 | 0.9 | 0.02 | 2.897 | 0.474 | 0.565 | 155 | 77 | 11.57 | 0.680 | 3.527 | 0.132 |
| 20 | 900 | 0.9 | 0.05 | 2.898 | 0.475 | 0.822 | 167 | 77 | 11.57 | 0.854 | 3.533 | 0.141 |
| 21 | 900 | 0.9 | 0.2 | 2.900 | 0.505 | 1.503 | 395 | 84 | 10.59 | 2.833 | 3.606 | 0.273 |
| 22 | 900 | 0.9 | 0.1 | 2.898 | 0.478 | 1.187 | 247 | 80 | 11.13 | 1.957 | 3.544 | 0.191 |
| 23 | 2,000 | 0.8 | 0.0 | 2.888 | 0.495 | 0.430 | 349 | 174 | 11.43 | 0.639 | 3.537 | 0.156 |
| 24 | 2,000 | 1.0 | 0.0 | 2.908 | 0.453 | 0.505 | 343 | 171 | 11.62 | 0.652 | 3.498 | 0.143 |

For runs 1–5, in increasing K, ApEn values are 0.165, 0.266, 0.442, 0.472, and 0.489, monotonically increasing with K. For the 900 point runs (6–10), corresponding ApEn values are 0.165, 0.262, 0.431, 0.495, and 0.510, again steadily increasing with K. With these longer runs, distinction is sharper between the K=0.8 case and the K=0.9 and K=1.0 cases. Furthermore, ApEn is (slightly) larger for the K=1.0 case than for the K=0.9 case, establishing system distinction despite the presence of chaos in both instances. In addition, the ApEn values remain nearly constant for run lengths greater than 900 points, as indicated by runs 23 and 24. For K=0.8, no noise, ApEn=0.431 with 900 points, while ApEn=0.430 with 2000 points; for K=1.0, no noise, ApEn= 0.510 with 900 points, while ApEn=0.505 with 2000 points. Hence for this model, (i) ApEn distinguishes all the versions from each other; (ii) ApEn, via monotonic increase, directly verifies the growing complexity and increased feedback with increased K; and (iii) establishes points (i) and (ii) with no more than 180 points necessary.

Runs 11–22 indicate the effects of noise on the ULTRA and ApEn computations. For each of the three versions K=0.7, K=0.8, and K=0.9, four different noise levels were examined, standard deviations of 0.02, 0.05, 0.1 and 0.2, corresponding to CVs of approximately 1%, 2%, 4%, and 8%, for 900 point time-series. ULTRA maintained its pulse count of roughly 80 total pulses throughout these runs, increasingly slightly with noise level of 0.2 to 83, 83, and 84 pulses for the K=0.7, K=0.8, and K=0.9 cases, respectively. As above, this provided little distinction among these three systems. At 0.02 noise, ApEn maintained increasing order with complexity (0.323 vs. 0.503 vs. 0.565); similarly for the 0.05 and 0.1 noise levels (0.633 vs. 0.761 vs. 0.822, 1.112 vs. 1.167 vs. 1.187). With the 0.1 level noise, the system distinctions were becoming blurred, and with 0.2 noise, the system distinctions were obliterated, especially in the K=0.8 vs. K=0.9 cases (1.453 vs. 1.544 vs. 1.503), in which complexity is slightly reversed (due to "realization" and finite sample size issues). This blurring is evident in phase portraits comparing the K=0.8 and K=0.9 cases at 0.2 noise (data not shown).

Figure 10A:
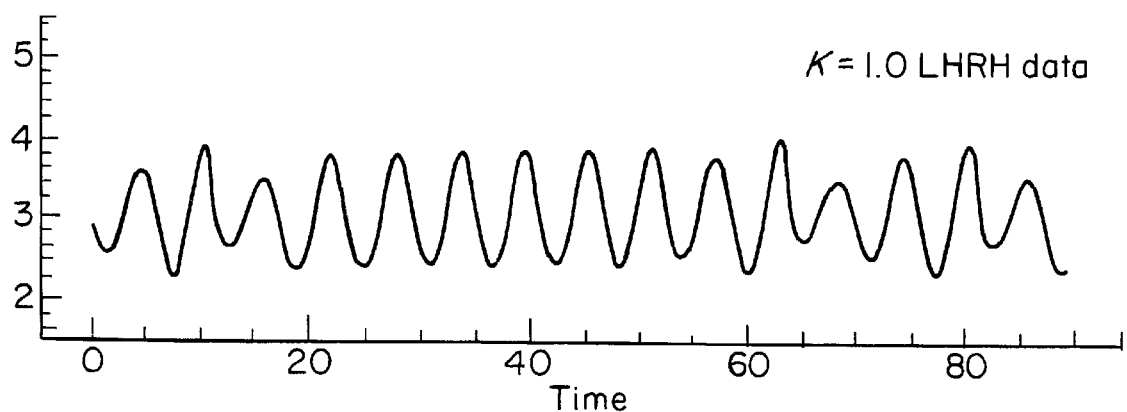
FIGS. 10A–C are Rossler coupled differential equation model time-series output for LHRH data, LH data, and testosterone data.
Figure 10B:
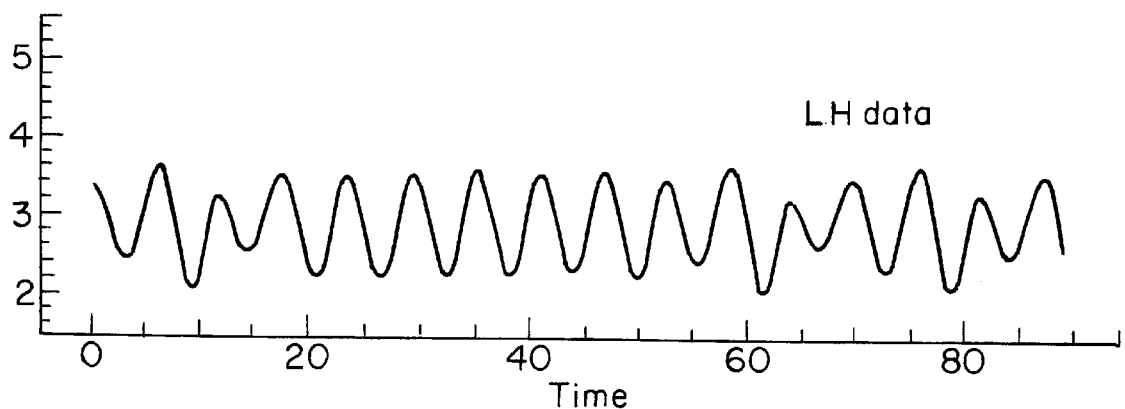
Figure 10C:
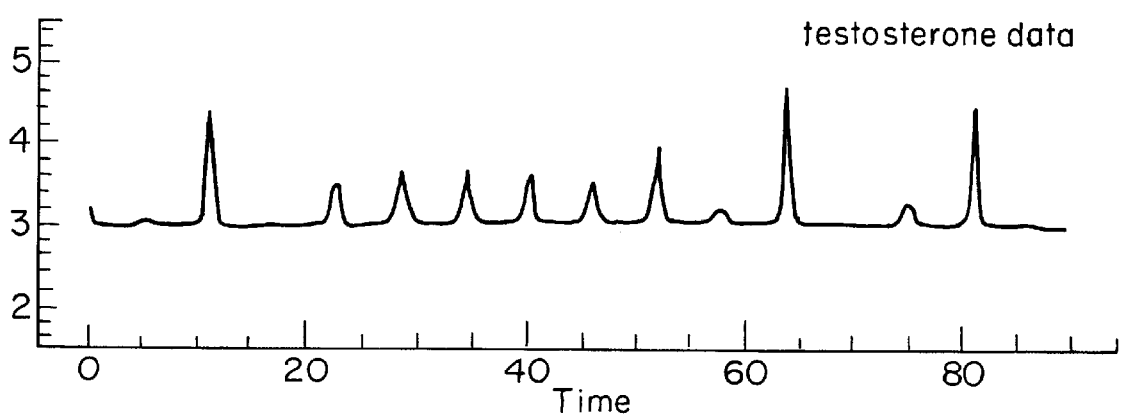

FIGS. 10A–C compares the LHRH, LH, and T time-series from the K=1.0 version of this model, and raises an important issue. The LHRH and LH time-series are visually similar; both have 16 pulses, similar amplitudes and general pulse characteristics. It could be expected that these hormones belong to a single autonomous system. The behavior of T, however, is visually discordant with the behavior of LHRH and LH; there are 12 pulses, long stretches of flat tracings, spiked pulses, and three pulses that are much greater in amplitude than the others. Thus, dissimilar pulsatile characteristics of hormonal plasma concentrations do not eliminate the possibility that the hormones may be derived from a single system, with no external influences.

Discussion and General Conclusions

Some general conclusions from the above runs can be inferred. ApEn and ULTRA provide different and complementary information from the data. ULTRA gives a first-order measure of the pulsatility of the system, via the pulse count and related statistics. ULTRA can be applied to data with 10% CV with 180 data points, typical values for current studies. For some systems, such as those defined by the Ueda and Rossler models above, ULTRA is relatively ineffective at distinguishing distinct versions of the systems, and may possibly give counterintuitive results. Subordinate pulses create difficulties for ULTRA, as do models in which pulse timing is reasonably constant, where the variation is in the patterned versus random behavior of the respective pulse amplitudes. The first-order, as opposed to finely-tuned behavior of ULTRA is further evidenced by the observation that in noiseless systems, ULTRA is statistically equivalent to a sign-change identifying algorithm. This algorithm was noted earlier to be useful, but to lack the greater versatility that appropriately weighted versions maintain.

In contrast, at low intra-assay noise levels, with the stated input parameters ApEn can effectively distinguish all the distinct versions of each model from one another. In directly assessing the regularity of the data, ApEn can distinguish between versions of episodic behavior, as well as between episodic versus more random behavior. By considering all the time-series data, not just the data that make-up the pulse acmes, ApEn evaluates subordinate behavior. There is a significant increase in ApEn with increasing CV, though it is still possible to compare systems with identical intraassay CVs, even as high as 8%, via ApEn to discern system distinction. Such analyses produce ApEn values that are much larger than the corresponding values in noiseless systems; in a few cases, systems that are distinguished by ApEn at low CV are no longer distinguished at 8% CV.

From the Ueda model, it is noted that there may be important regularity information in time-series data that can be effectively extracted only in the presence of a small intra-assay CV. For such purposes, ApEn is well suited, with a finer focus than that of the pulse-detection algorithms currently employed. The required decrease in intraassay CV from current levels is consistent with the direction in which endocrinologists are actively moving.

To validate the above claim of effective distinction of model versions by ApEn, an estimate of ApEn standard deviation is determined. The estimate (Monte Carlo estimates, 100 replications per computed standard deviation) is provided for two quite different processes: the MIX(p) model introduced in Pincus (Pincus, S. M., "Approximate Entropy as a Measure of System Complexity," *Proc. Natl. Acad. Sci*. 88 (1991):2297–2301) and a paradigm for chaos, the parametrized logistic map, $f_a(x)=ax(1-x)$, $3.5<a<4.0$. First define MIX(p):fix $0 \leq p \leq 1$. Define $X_j=\sqrt{2} \sin(2\pi j/12)$ for all j, $Y_j$=IID (Independent, Identically Distributed) uniform random variables on $[-\sqrt{3}, \sqrt{3}]$, and $Z_j$=IID random variables, $Z_j=1$ with probability p, $Z_j=0$ with probability 1-p. Then define $MIX(p)_j=(1-Z_j)X_j+Z_jY_j$. This is a family of stochastic processes that samples a sine wave for p=0, is IID uniform for p=1, and intuitively becomes more "random" as p increases. For m=2, r=20% of the process standard deviation, and 900 points, the standard deviation of ApEn (MIX(p)), calculated for each 40 values of p equally spaced between 0 and 1, is less than 0.055 for all p. For 180 points, ApEn (same m and r) standard deviation is less than 0.07 for all p.

For the logistic map, the "randomization" needed to make this deterministic map fit a Monte Carlo scenario is given by different choices for the initial condition. For m=2, r=20% of the process standard deviation, and 900 points, the standard deviation of ApEn ($f_a(x)$), calculated for each of 50 values of "a" equally spaced between 3.5 and 4.0, is less than 0.015 for all a. For 180 points, ApEn (same m and r) standard deviation is less than 0.035 for all a. Thus ApEn values of a=1.1 and b=0.9 would have very high probability of coming from different processes, for either of these two model classes. The MIX process computation is appealing, in that the process is nearly IID (uncorrelated iterates) for p near 1. Because larger ApEn standard deviation generally corresponds to more uncorrelated processes, it is expected that the standard deviation bounds for ApEn for MIX(p) will provide bounds for a large class of deterministic and stochastic processes.

Given the ApEn sensitivity to intra-assay CV, several caveats must be noted to ensure appropriate application of this method. If the same process is analyzed in two different laboratories, one with CV 2%, the other with CV 8%, the ApEn values can be significantly different. Also, if the same process is analyzed under two very different sampling regimens (e.g., samplings every 5 minutes, versus every 20 minutes), ApEn values can be quite different; in effect, the relative noise levels can be dissimilar. Thus, until CVs and other "noise levels" that vary from system to system are markedly reduced from present values, comparison of ApEn values should be restricted to data sets produced from similar settings (e.g., same laboratory and sampling frequency), which would ensure a relatively constant CV across samples. The comparisons done for the two models above, at a fixed CV level, model such a "homogeneously noise" environment, and as already noted, show valid ApEn distinction, given CVs at presently observed levels.

Along the same lines, it is critical to distinguish between the comparison of ApEn (with fixed m and r) values for two data sets, given N data points, from the questions of convergence of ApEn for a specific system. The results from the two models analyzed above indicate that ApEn typically needed on the order of 900 points for convergence. In comparing systems with 180 data samples, ApEn distinguished most systems that were distinguished with 900 points, occasionally less sharply. Thus, a fixed sample length should be used for all data sets under study.

The models analyzed above were chosen to illustrate different types of physiologically plausible behavior, and while there was no substantial effort to model a particular endocrine system, it would seem likely that a true endocrine system would be at least as mathematically complex as either of these models. Thus it is imperative that statistics, meant to evaluate pulses generated by true endocrine system hormones, be capable of effective discrimination of versions of the above models. A key observation from these models is that nonlinear systems can produce highly nontrivial, episodic, yet non-periodic output behavior from equations that are simple in appearance. Output that appears as a sequence of identical, sine wave-like pulses is usually associated with uncoupled, linear systems. Such linear systems have been extensively studied because they readily yield exact, analytic mathematical solutions. There is no a priori reason to anticipate that true endocrine systems be either linear or devoid of feedback. Hence, the likelihood that episodicity (no exactly repeating patterns) is physiologically normative must be considered.

In addition to those considered above, stochastic models, such as Markov processes and networks of queues, could have been analyzed. Similar qualitative conclusions to those realized herein are anticipated.

In complex systems of glands and hormones, a direct barometer of feedback, or interaction between systems would likely be insightful. Either a breakdown in or an excessive amount of feedback may mark the onset of disease, and a method that could directly mark such a change in feedback has added value. For the Rossler model, as the coupling parameter K was increased, ApEn steadily increased, thus providing a direct measure of increasing system complexity. In general, ApEn appears to increase with greater system coupling and greater attendant complexity. While coupled systems currently must be individually analyzed to ensure this increase of ApEn with feedback parameter, this property holds significant potential utility in practical applications.

Above, potential near-term applicability was indicated, by observing that with 180 points, or with 8% CV, ApEn still was useful in drawing distinctions between most model versions. In a preferred embodiment of the invention, a randomized version of ApEn is applied to hormone level data. This randomized version of ApEn has the advantage that it can be coupled with bootstrapping methods (Efron, B., *The Jacknife, the Bootstrap, and Other Resampling Plans*, Philadelphia:SIAM, 1982:27–36) to yield a statistic that distinguishes data sets of 100 points with high probability (via a small variance), in the presence of nontrivial noise. Hence, greater applicability of ApEn to hormone level data can be achieved both by more accurate and numerous clinical data, and by statistical advances outside the clinical setting.

In summary, the potential use of approximate entropoxy (ApEn) to quantify regularity in endocrine hormone data has been described. ApEn offers new insights in the detection of abnormal behavior, especially given modest increases in the number of data samples and in the accuracy of the serum concentration level at each sampling.

Turbulence Measurement and Flow Control

When a fluid impinges on an object, the undisturbed fluid pressure and the velocity of the fluid changes. Depending on the shape of the object, a wake may be formed, which sheds eddies. The eddies may be aperiodic or periodic. The formation of wakes is dependent on the Reynolds number, which is a dimensionless ratio of the inertial force to the viscous force of the fluid.

An object in a fluid stream may be subject to the downstream shedding of vortices from alternating sides of the upstream object. As the wake frequency approaches the natural frequency of the structure, the periodic lift force increases asymptotically in magnitude. When resonance occurs, the structure fails. The neglection of this phenomenon has accounted for failures of numerous structures, including electric transmission lines, smokestacks, and bridges.

Turbulence also affects the amount of fraction or drag between the object and the medium. As the fluid flow transitions from laminar to turbulent, the coefficient of drag increases. Increased drag results in inefficient flow of the medium past the object. The inefficiency caused by turbulence requires that additional energy be exerted to maintain the flow of the medium. For example, a vehicle (or vessel) in motion consumes more fuel when the air flow (or water flow) in the wake is turbulent instead of laminar. Hence, it is desirable to maintain laminar flow as long as possible.

A preferred embodiment of the invention uses a negative feedback system to create maximum or minimum turbulence of a fluid flowing around a primary solid. Classical control or optimum control techniques are used. A secondary solid, smaller than the primary solid is placed in the fluid in such a fashion as to either encourage or discourage turbulence. The turbulence is controlled by critically pulsing, shaping, slowing or otherwise metering the fluid. The system can be adjusted for a small amount of turbulence that minimizes stress on the surface of the primary solid while maximizing flow, or any other complex combination of variables with a desired result.

Figure 11:
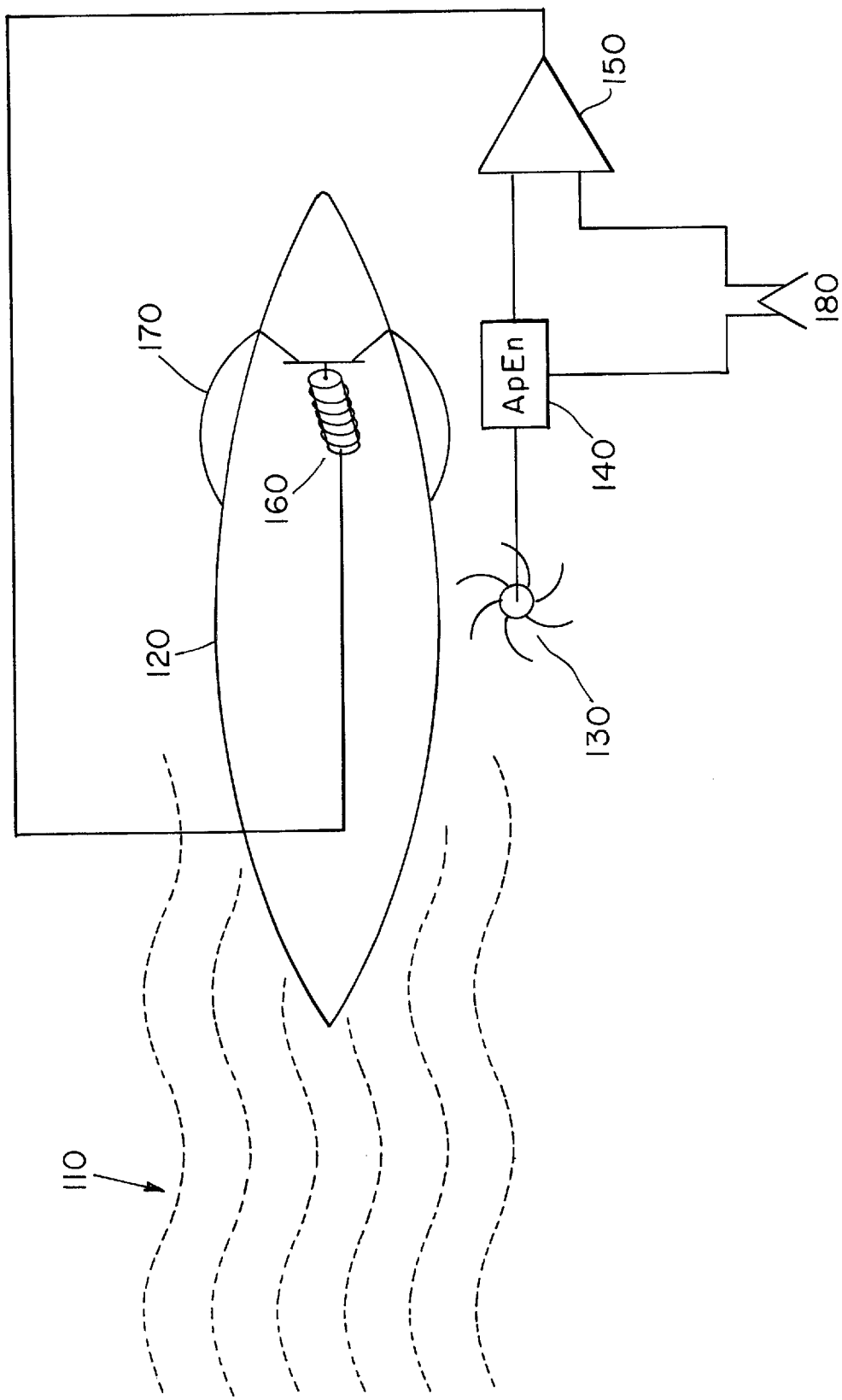
FIG. 11 is a schematic block diagram of a preferred embodiment of a turbulence measurement and flow control device.

FIG. 11 is a schematic block diagram of a preferred embodiment of a turbulence measurement and flow control device according to the present invention. A medium 110, such as a fluid or a gas, is shown flowing across or through a region constrained by a primary solid 120. The medium 110 includes but is not limited to air, water, and blood. The primary solid 120 may be an airfoil or a hydrofoil (e.g. a wing, a propeller blade, or a rudder), a valve, a tube, a pipe, a channel, or any other structure that partially interferes with the flow of the medium 110. In particular, the primary solid 120 may be an artificial heart valve. The flow parameters of the medium 110 are measured by at least one sensor 130. The sensors 130 detect and quantify parameters such as speed, pressure, and direction of flow at specific locations in proximity to the primary solid 120.

The measured parameters from sensors 130 are provided to a computational unit 140, which employs digital computations of approximate entropy to determine a time-varying parameter ApEn(t) for the medium 110 in proximity to the primary solid 120. The ApEn(t) parameter is continuously provided to a compensated negative feedback control 150.

The system uses ApEn as a time-varying measure of turbulence, rather than the classical Reynolds Number, because ApEn is easier to measure, more immune to measurement noise and error, scale length independent, and completely shape independent.

The feedback control 150 generates an optimum time-varying signal to provide to an actuator 160. The actuator 160 moves a secondary solid 170. The secondary solid 170 may be a constrictor, a flap, a vibrating plate, or any other structure that affects the flow of the medium 110, so as to change and optimize the flow characteristics of the medium 110 in proximity to the primary solid 120. In a stagnate medium, the approximate entropy will equal zero. Increasing turbulence is indicated by an increasing value for approximate entropy. The optimum time-varying signal will attempt to either converge ApEn(t)=0 to reduce turbulence or diverge ApEn(t)>0 to increase turbulence.

Auxiliary inputs 180 to the computational unit 140 and to the feedback control 150 provide manual adjustment of desired flow characteristics, so an alternate parameter can be optimized. The alternate parameters may be a combined function of the magnitude of turbulence, the flow speed, and the pressure.

Assessment of DNA Sequences

Approximate entropy (ApEn) can also be directly applied to quantify or associate measures of irregularity of deoxyribonucleic acid (DNA) sequences. DNA is a series of amino acids, which are identified in the DNA sequence using the letters A, C, G and T. The sequence can be very short or very long. Each of these letters can be assigned a different integer value between 1 and 4, inclusive. For example, A=1, C=2, G=3, and T=4. As such, the DNA sequence "AACGGTT-TAAT . . . " can be rewritten as "11233444114 . . .". DNA sequences are typically provided in either man-readable or machine-readable format.

Figure 12:
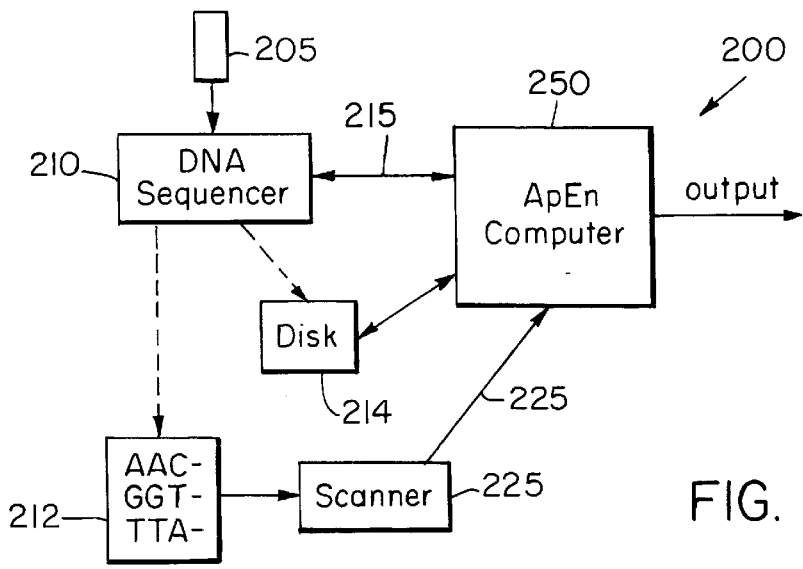
FIG. 12 is a schematic diagram of a computing system for assessing DNA sequences.

FIG. 12 is a schematic diagram of a computing system for assessing DNA sequences. The system 200 includes a DNA sequencer 210 in communication with an ApEn computer 250 over a communication link 215. The ApEn computer 250 can be any specific or general purpose computer for computing approximate entropy from the DNA sequence. Although the ApEn computer 250 is illustrated as being separate from the DNA sequence 210, they can be integrated together. A DNA sample is labelled with radioactive material and a sequencing gel 205 is produced using well-known techniques. The DNA sequencer 210 includes a laser scanner to read the sequencing gel 205 representing the sequence of amino acids in the DNA of the sample. Conventional scans of DNA sequences, however, are prone to error. Consequently, most sequencing gels are manually read and transcribed into a sequence listing.

In a preferred embodiment of the invention, a digital data stream representing the DNA sequence read from the gel 205 is generated by the DNA sequencer 210 and transmitted to the ApEn computer 250 over the communication link 215 for real-time evaluation. Alternatively, a man-readable paper listing 212 or a machine-readable disk 214 having the DNA sequence can be automatically generated by the DNA sequencer 210 or manually produced. The listing 212 or disk 214 facilitates off-line or remote evaluation of the DNA sequence. The paper listing 212 is preferably converted to a machine-readable form by a scanner 220 connected to the ApEn computer by a serial cable 225 or by manual entry of the data. The disk 214 can be read by the ApEn computer 250 using a disk drive.

A value for ApEn can now be calculated by the ApEn computer 250 for any (and all) window lengths m, where r<1 (e.g., r=0.5). Thus the ApEn computer can look for exact subpattern matches of length m, and the persistence, or conversely, lack of repetitiveness of same. Once m increases to above about 3 or 4 in ApEn(m) computations, the sequences that ApEn(m) detects as atypical may not be readily detected by cursory, or even studied human inspection. For example, one or two aberrant length 8 sequences (i.e., m=8) somewhere in a DNA sequence of length 1,000,000 are difficult to catch by manual study.

The application of ApEn to assessing DNA sequences are myriad, including the detection of abnormal sequences which may indicate altered genes. That is, assessing sequential irregularity of and subpatterns within the DNA sequence, the DNA itself can be assessed and acted on as appropriate. In addition, ApEn can be used to verify that DNA has been correctly sequenced by automatically checking the DNA sequence for errors. For example, questionable sections of the sequence can be returned to the DNA sequencer 210 over the communication link 215 where the sequencing gel can be rescanned or manually checked to verify the accuracy of the DNA sequence. By using a feed-back loop, ApEn can be used in a more accurate automated DNA sequencing system, thus reducing or eliminating human labor in DNA sequencing.

Application to Financial Time Series Data

Several economists have studied the application of "chaos" algorithms to actual financial data, and have generally concluded that (i) there may be some evidence of sequential correlation in the time-series, but (ii) these algorithms have unsatisfactory statistical properties, and thus any quantitative conclusions must be lightly regarded. It has been noted that actual error bars for these "statistics" are quite large, and that there is substantial bias in dimension algorithms with small (typically sized) data sets. Athough others have applied these algorithms to distinguish random from deterministic systems, they conclude that evidence for chaos in post-war quarterly GNP data is weak. Stock return data, however, may not be incompatible with a model where some of the variation comes from nonlinearities, as opposed to randomness. It has also been suggested that while there is strong evidence to reject the hypothesis of IID (totally random) stock returns, the cause does not appear to be either regime changes or chaotic dynamics; rather, the cause appears to be conditional heteroskedasticity.

In accordance witht the invention, ApEn was applied to stock market data to test the validity of the (null hypothesis) log-normal, independent increment assumption for returns, common to many models. Standard & Poor (S&P) 500 (SPX) index data from 22 distinct 1000 point periods was analyzed for the years 1987–1988. The input time-series $\{s_i\}$ were sequences of prices taken at 10 minute intervals, obtained daily from the opening quotation at 9:30 A.M to the closing quotation at 4 P.M; thus 25 business day contiguous blocks were required to comprise each 1000-point period. The interest was in incremental returns, and hence to evaluate the null hypothesis, ApEn was applied to the time-series $\{u_i\}$ defined by $u_i=\log(s_{i+1}/s_i)$. During 1987–1988, the $\{u_i\}$ time-series had a standard deviation of approximately 0.002; following the guidelines given above, ApEn(2, 0.0005, 1000) was calculated.

Recall that if the $\{u_i\}$ are an IID process of (normal) random variables, the expected value of the parameter ApEn(m,r) can be analytically computed. This is for an IID process with density function f(x), with probability 1, for any m, $$ApEn(m, r) = -\int f(y)\log\left(\int_{z=y+r}^{z=y-r} f(z)dz\right) dy. \quad (7)$$

Note that Equation 7 is independent of m; this fact can be used to reject the IID hypothesis in settings with abundant data, as indicated below. For the lognormal return hypothesis under consideration, Equation 7 is calculated by setting f(x)=N(m,s), the normal density with specified mean and standard deviation. As a minor nuisance, the log term inside the integral prevents simple analytic calculations in general, requiring straightforward numerical calculations instead.

However, to compare actual ApEn computations from data to theoretical calculations, it is crucial to remember that ApEn(m,r,N) provides a biased estimate of ApEn(m,r). Thus it is inappropriate to compare ApEn (2, 0.0005, 1000) values to the ApEn(m,r) calculations. Instead, a Monte Carlo generation (50 replications per time-period) of 1000 IID normally distributed values of specified mean and standard deviation was performed to match those from each (of the 22) empirically derived $\{u_i\}$ time-series. ApEn(2, 0.0005, 1000) of this series was then computed. These ApEn values were compared to those from observed data. If the null hypothesis that SPX returns $\{u_i\}$ are independent normal random variables were valid, ApEn values from the Monte Carlo sequences should nearly match the ApEn values from the $\{u_i\}$ derived from the actual time-series.

The average ApEn value calculated from data was 1.098, while the average ApEn value calculated from the theoretical Monte Carlo replications assuming the null hypothesis was 1.491. Furthermore, in all but one time-period, the actual ApEn value was at least 0.3 less than that computed assuming the null hypothesis. For IID normal random variables with standard deviation given by that of $\{u_i\}$ as empirically determined, the standard deviation of ApEn(2, 0.0005, 1000) is between 0.02 and 0.05 (Monte Carlo simulations), consistent with error bars noted in an earlier section. Thus in 21 of the 22 time-periods under study, the theoretical ApEn value given the null hypothesis is at least six ApEn standard deviations away from the calculated values from data, resulting in clearcut rejection of this hypothesis. As well, it is particularly notable that the one time period where theoretical and calculated ApEn values nearly agreed was Oct. 1, 1987–Nov. 5, 1987, the period covering the October 1987 stock market crash. Additionally, analogous calculations based on 5 minute and 20 minute returns produce very similar results, nearly 30% smaller computed ApEn values than those calculated from a lognormal IID assumption during all but the "crash" time-period. This study verifies the application of ApEn to financial market data.

Though not directly studied above, it is further anticipated that ApEn could provide an economic indicator of change, independent of model considerations. Because ApEn is a marker of stability, change in its value could potentially forecast changing market conditions. Thus an investor might be advised to expect greater market instability, and might accordingly take a more cautious stance in financial decisions. As indicated above, the only time-period of the 22 tested epochs for which empirical ApEn was as large as that for IID lognormal returns was the time-interval around the 1987 stock-market crash.

Cross-ApEn

Cross-ApEn is preferably utilized to quantify asynchrony or conditional irregularity. Cross-ApEn can be employed to compare sequences from two distinct yet intertwined variables in a network. Specifically, cross-ApEn aggregates low-order, two-variable joint distribution at moderately course resolution. In accordance with the invention, cross-ApEn is employed to directly assess network, not just nodal, evolution such as uncoupling and changes in feedback or control. The precise definition, given next, is thematically similar to that for ApEn.

Figure 13:
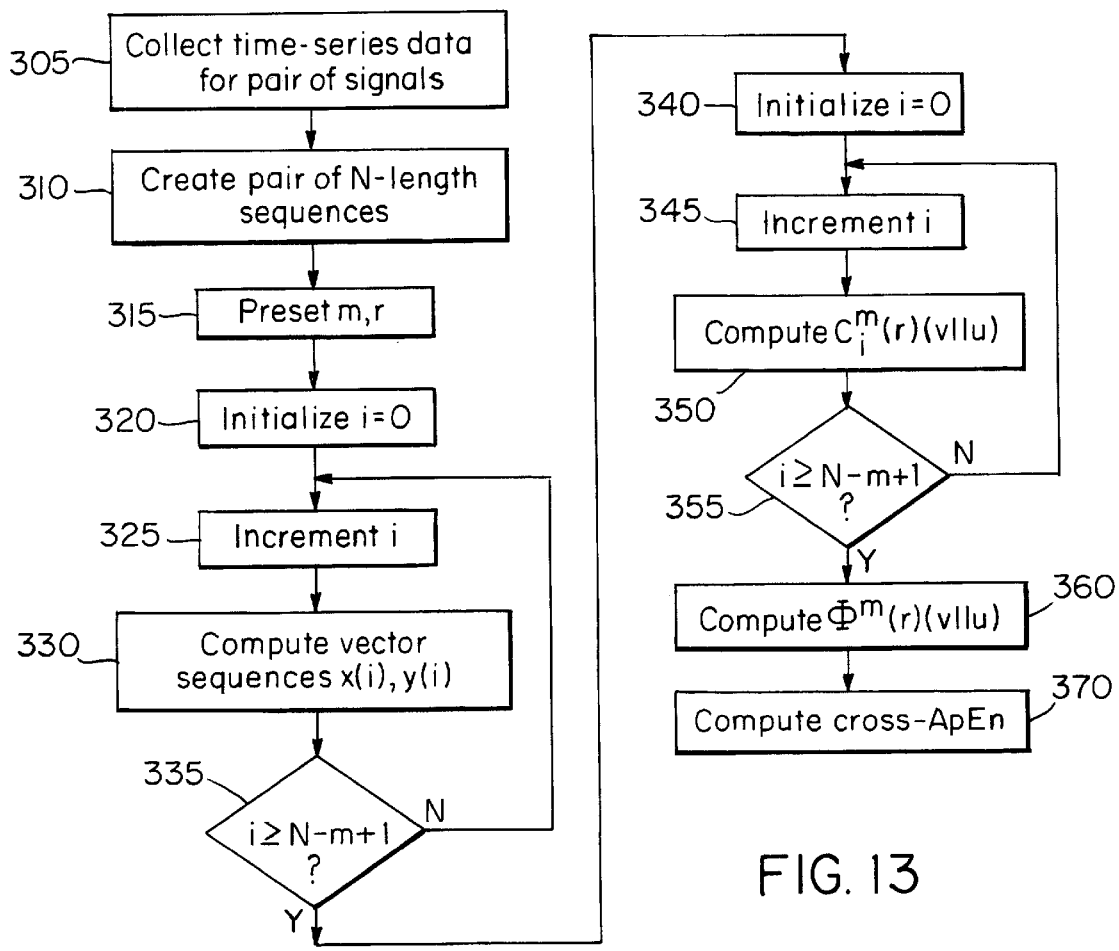
FIG. 13 is a flow chart for calculating a measure of cross-ApEn.

FIG. 13 is a flow chart for calculating cross-ApEn. First, time-series data from a pair of signals is collected at step 305. The paired signal inputs can be from within a traditional network or from less obviously related, broader networks. Two sequences u=(u(1), u(2), ... u(N)) and v=(v(1), v(2), ... v(N)) are assigned at step 310. Although, for illustrative purposes, each sequence is of length N, the sequences can have different lengths with slight modifications being made to the equations. Each series can also be derived from distinct sampling frequencies because cross-ApEn does not attempt to finely reconstruct joint measure. Discrimination between signals only requires a fixed protocol be followed throughout. The input parameters m for the window width and r for the tolerance (both described above) are fixed to predetermined values at step 315.

At step 320 an index variable i is initialized to zero. At step 325, the index variable i is incremented. Next, vector sequences x(i)=(u(i), u(i+1), ... u(i+m-1)) and y(j)=(v(j), v(j+1), ... v(j+m-1)) are formed from u and v, respectively, at step 330. At step 335, the process loops back to step 315 until the index variable i equals N-m+1.

Upon exiting the loop, the index variable i is reinitialized to zero at step 340. At step 345, the index variable i is incremented. Then, at step 350, $C_i^m(r)(v\|u)$ is computed to be (the number of $j \leq N-m+1$ such that $d[x(i), y(j)] \leq r$)/(N-m+1), where $d[x(i), y(j)] = \max_{k=1,2,\ldots,m}(|u(i+k-1)-v(j+k-1)|)$, i.e., the maximum difference in their respective scalar components. At step 355, the process loops back to step 345 until the index variable i reaches N-m+1. The $C_i^m(r)$'s measure, within a tolerance r, the regularity or frequency of v-patterns similar to a given u-pattern of window length m.

At step 360, $\Phi^m(r)(v\|u)$ is computed as the average value of $\ln C_i^m(r)(v\|u)$. That is, $$\Phi^m(r)(v\|u) = \frac{1}{N-m+1} \sum_{i=1}^{N-m+1} \ln C_i^m(r)(v\|u). \quad (8)$$

Finally, at step 370, cross-ApEn is computed as $$\text{cross-ApEn}(m,r,N)(v\|u) = \Phi^m(r)(v\|u) - \Phi^{m+1}(r)(v\|u). \quad (9)$$

The fewer the number of subpattern matches between the paired time-series data, the greater is the asynchrony between the time-series data, indicated by larger cross-ApEn values.

Representative Application of Cross-ApEn

As a representative application of ApEn and cross-Apen, a study was performed to apply ApEn and cross-ApEn to hormonal time-series data. Greater understanding of the evolution of the hypothalamo-pituitary-testicular axis with aging is of vital importance both scientifically, in elucidating the physiology of reproductive capacity, and clinically, in assessing, e.g., a loss of libido, or decreased reproductive performance. In recent years, there has been considerable study of LH and testosterone serum concentration time-series in both younger and older males, both to develop such understanding, and to determine whether a hypothesized male climacteric (or so-called andropause) at least partially analogous to menopause in the female exists, and if so, in what precise sense. Such studies have evaluated changes in (i) mean concentrations of total and free testosterone, and LH and the ratio of biological to immunological (B/I) LH activity; (ii) "near-term" (circhoral) pulsatility characteristics of LH and testosterone, via changes in mean frequencies and amplitudes; (iii) "longer term", i.e., nyctohemeral characteristics of LH and testosterone release. While considerable insight has already been gained from such studies, there remain nontrivial controversies concerning several classes of findings, e.g., primary determinations of whether overall mean levels of LH and testosterone decrease with increasing age. Furthermore, biologically, the precise neuroendocrine mechanisms that underlie such age-related changes remain largely unresolved.

In accordance with a preferred embodiment of the invention, possible reproductive aging changes are examined from two separate perspectives. In particular, the degree of irregularity of each of the LH and testosterone time-series is directly evaluated, via ApEn, and the degree of asynchrony in the joint LH-testosterone series is directly evaluated, via cross-ApEn. Data collected by frequent venous sampling (every 2.5 minutes) overnight was analyzed to delineate the nature of changes in the secretion of these two hormones in healthy older men.

A study group was established form 14 young (age 21-34 yr) and 11 aged (age 62-74 yr) healthy nonsmoking men within 20% of ideal body weight. For each subject, blood samples were obtained during a sleep period on a second night of study, at 2.5 minute intervals commencing at 2300 hours, with sampling terminated when the subject spontaneously awakened, for an average sampling duration of 7 hours. Serum LH concentrations were measured in duplicate by using a two-site monoclonal immunoradiometric assay available from Nichols Institute, San Juan Capistrano, California. Assay sensitivity was 0.2 IU/L according to the First International Reference Preparation. Serum total testosterone concentrations were quantified in duplicate for each sample by using a solid-phase RIA available from Diagnostic Products, Los Angeles, California. Assay sensitivity was 20 ng/dL. For both LH and testosterone assays, intra- and interassay imprecision was less than 10%.

In this study, ApEn(m,r) values were calculated for all data sets, m=1 and r=20% of the standard deviation (SD) of the individual subject's hormone time-series. Normalizing r to each time-series SD gives ApEn a translation- and scale-invariance to absolute serum concentration levels, hence, e.g., ApEn has identical values for a time-series and its standardized (centered and normalized) counterpart.

All statistical comparisons made below employ the two-sided t-test, with unknown variance, except for the ApEn (LH) vs. ApEn(testosterone) comparisons within each of the younger and older cohorts, for which we employed the paired t-test. Results are given as mean +/- standard deviation.

Figure 14A:
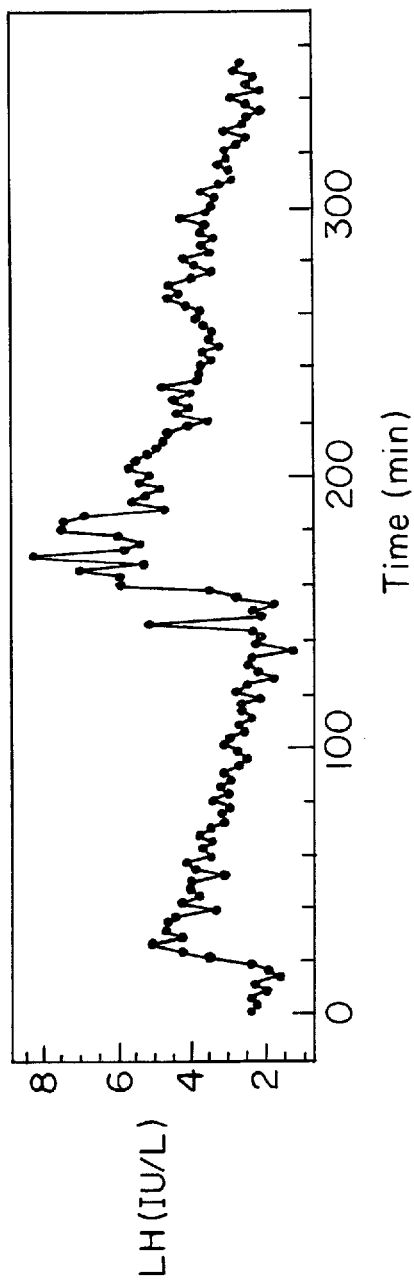
FIGS. 14A–14B are representative serum hormone concentration time-series of LH and testosterone data, respectively, for a young subject.
Figure 14B:
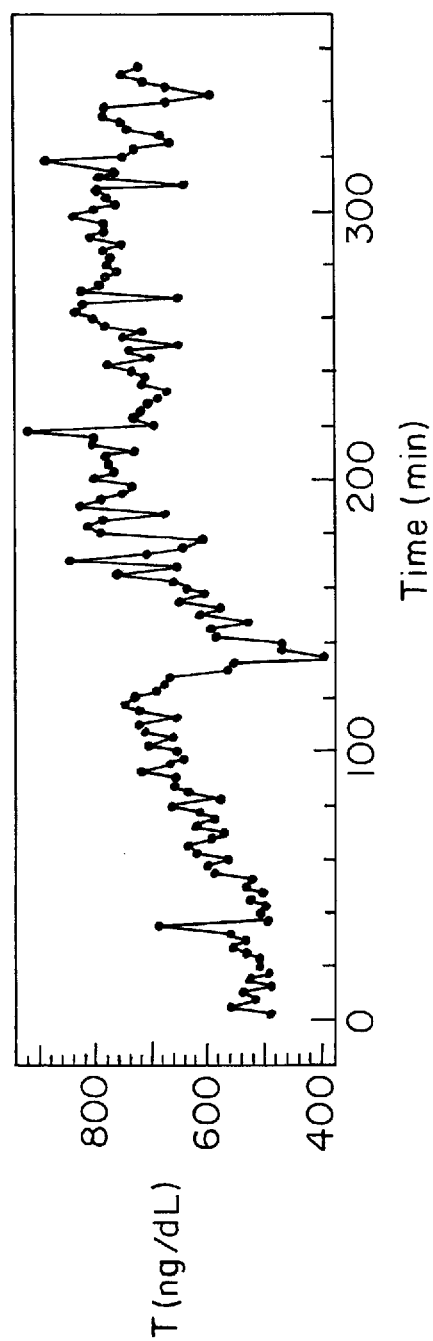

FIGS. 14A-14B are representative serum hormone concentration time-series of LH and testosterone data, respectively, for a young subject. FIGS. 15A-15B are representative serum hormone concentration time-series of LH and testosterone data, respectively, for an aged subject. Inspection of these profiles suggests that clear pulse identification is a nontrivial endeavor, especially for the aged subjects' testosterone series. Serum LH (in IU/L) and testosterone (in ng/dL) concentrations were measured in blood collected at 2.5 minute intervals during sleep in young and older subjects. Respective mean concentrations and ApEn(1, 20% SD) values were calculated as follows. For younger subjects, mean LH=3.68, ApEn(LH)=1.168, mean testosterone=680.1, and ApEn(testosterone)=1.495. In aged subjects, mean LH=2.48, ApEn(LH)=1.784, mean testosterone =353.0, and ApEn(testosterone)=1.678. Thus ApEn elucidates the differences in these time-series which are not so readily apparent to the eye, suggesting the ability to distinguish younger from older cohorts.

Figure 16B:
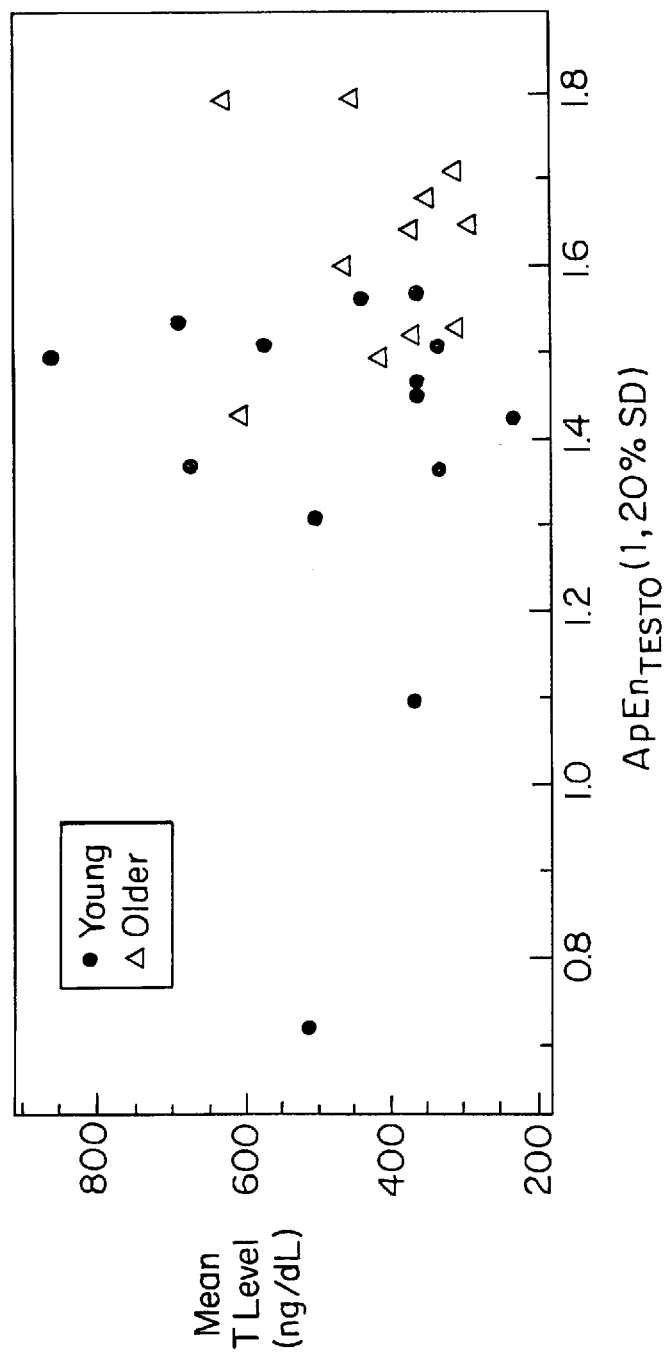

FIGS. 16A-16B are scatterplots of mean LH level vs. ApEn(LH) and of mean testosterone level vs. ApEn (testosterone), respectively. The scatterplots visually confirm an objective statistical distinction. Although mean (and standard deviation) LH and testosterone concentrations were indistinguishable in the 2 age groups (P>0.25), for LH, aged subjects had greater ApEn values (1.525 +/−0.221) than younger individuals (1.207+/−0.252), P<0.003, indicating more irregular secretion in the older cohort. For testosterone, aged subjects also had greater ApEn values (1.622+/−0.120) than younger counterparts (1.384+/−0.228), P<0.004. In young, but not older men, ApEn(testosterone) significantly exceeded ApEn(LH), P<0.02.

Quantitatively, the decision rule that associates ApEn(LH) values greater than 1.445 with aged subjects has a specificity of 93% and a sensitivity of 82%, while the decision rule that associates ApEn(testosterone) values greater than 1.60 with aged subjects has a specificity of 100% and a sensitivity of 64%. Notably, there was no difference in mean serum LH levels between the younger (2.409 +/−0.658 IU/L) and aged subjects (2.830+/−1.064 IU/L) levels, P=0.26; and there was no difference in mean testosterone levels between the younger (459+/−148 ng/dL) and aged subjects (415+/−115 ng/dL) levels, P=0.41.

Figure 17:
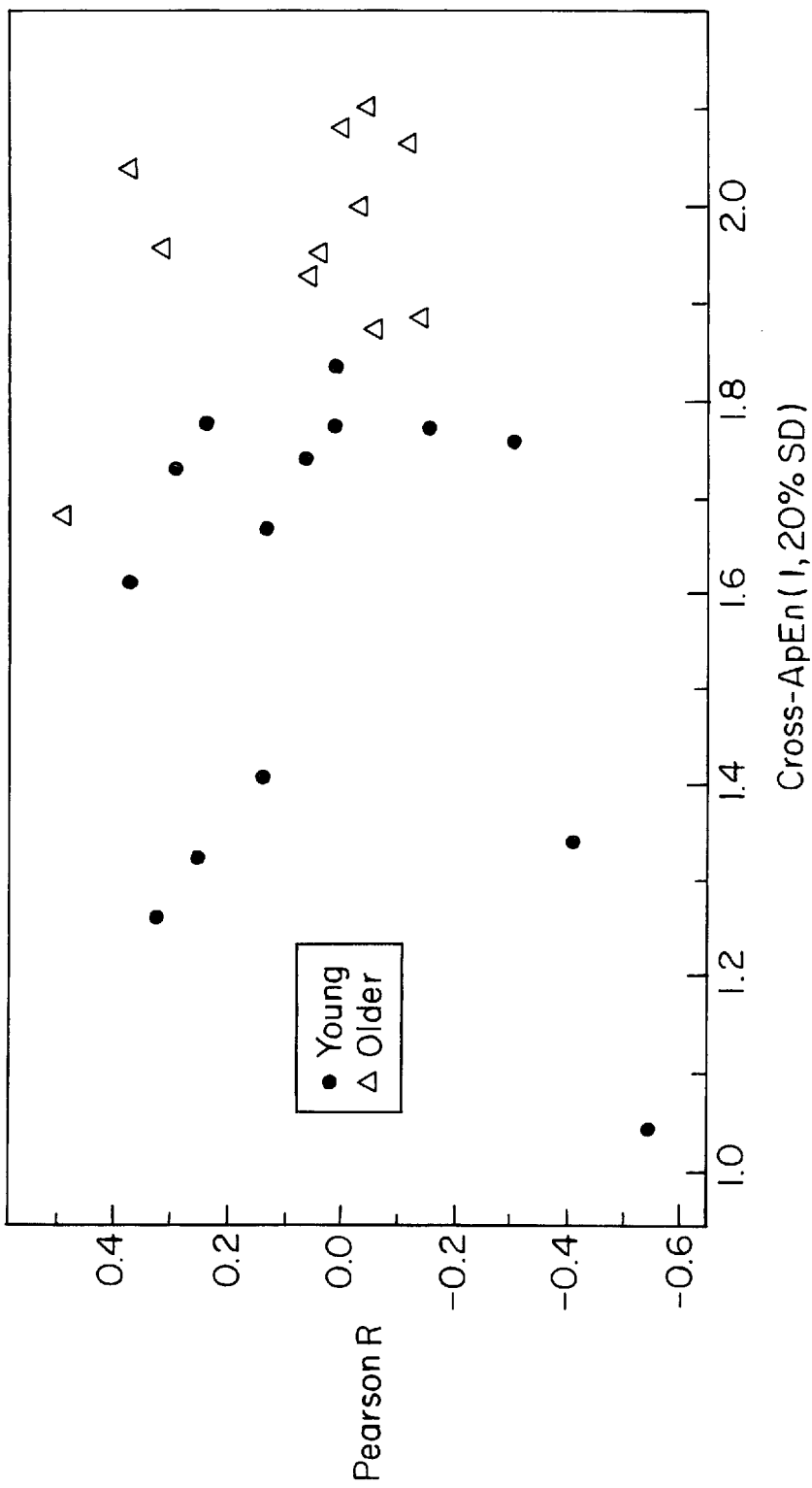
FIG. 17 is a plot of cross-ApEn values versus cross-correlation for the data of FIGS. 16A–16B.

FIG. 17 is a plot of cross-ApEn values versus cross-correlation for the data of FIGS. 16A–16B. Aged subjects had greater cross-ApEn values (1.961+/−0.121) than younger subjects (1.574+/−0.249), P<$10^{-4}$. Importantly, there was nearly complete separation of younger and older subject cross-ApEn values with all younger subjects' cross-ApEn values smaller than all but a single older subject's value. Alternatively, the decision rule that associates cross-ApEn values greater than 1.85 with aged subjects has a specificity of 100% and a sensitivity of 91%, indicating greater LH-testosterone asynchrony in the older group. In conjunction with previous findings of greater irregularity of GH release with increasing age, increased secretory irregularity with advancing age may be a widespread hormonal phenomenon. In counterpoint, cross-correlation (Pearson "R"), reveals no significant differences, either in the Pearson R-values directly, older subjects (0.078+/−0.210) vs. younger subjects (0.030+/−0.284), P=0.629; or in the magnitude of the correlation, assessed by |Pearson R|, older subjects (0.150+/−0.162) vs. younger subjects (0.231+/−0.155), P=0.220.

Summarizing the primary statistical results, for each of LH and testosterone, older males have consistently and significantly more irregular serum reproductive-hormone concentrations than younger males. The distinction between ApEn(testosterone) and ApEn(LH) indicating greater irregularity of the former in young men was lost in older men. Furthermore, cross-ApEn gives strong quantitative support to a mechanistic hypothesis, a loss of synchrony with aging in the coupled LH-testosterone system. This latter (cross-ApEn) finding reinforces the utility of studying network aspects, in addition to single-variable or nodal aspects, of hormone systems, both in statistical analysis and in modelling, and ultimately, in proposing and assessing therapies. The determinations that mean serum LH and testosterone concentrations in the young and older males were not significantly different, nor were linear cross-correlations, further suggest the need for the distinct perspectives assessed by quantification of irregularity and (a)synchrony.

It is expected that greater secretory irregularity, and possibly greater asynchrony, with increased aging may be a more general paradigm for many hormones, potentially indicating a diminution of subsystem integrity or of (synchronous) control.

It seems worthwhile to qualitatively compare the results above for the male to corresponding findings for the female, although sex-steroid levels decline more markedly in postmenopausal individuals than in aging men. Any analogies or comparisons between male and female evolution of "reproductive" hormone secretion as a function of increasing age are, of course, at best partial, given the irreversible cessation of female reproductive capacity in the aged, in contrast to continued, albeit diminished male fertility in advanced age. However, the above findings indicate distinct quantitative shifts in male hormonal secretory dynamics with aging.

In principle, there are several possibilities for the source of the erosion of LH-testosterone synchrony quantified above. These include: (i) decreased multi-synaptic modulation or synchrony of the hypothalamic GnRH neuronal network that produces the GNRH drive to pituitary LH synthesis and secretion; (ii) altered feedback control of individual or coupled GnRH-LH secretory activity by gonadal (steroid and non-steroid) hormones, via a disrupted feedback signal, e.g., of testosterone itself, or deficient responsiveness to the feedback signal; (iii) decreased GnRH and non-GnRH-dependent paracrine or autocrine coordination of LH secretion by gonadotroph cells; or (iv) disruption of effective (LH-testosterone) stimulus-secretion coupling at the level of the Leydig cell in the testis. Further physiological studies would be required to clarify the precise mechanistic basis of this change in the extent of asynchrony, as the present data do not distinguish among these theoretical possibilities. Nonetheless, because there is increased ApEn of LH release after short-term ketoconazole treatment in young men when testosterone secretion falls, and increased ApEn of GH release with fasting as IGF-1 falls, decreased feedback signal strength, or diminished GnRH-LH system responsiveness to any given feedback signal intensity, is favored as a unifying hypothesis.

The present findings provide an entirely distinct and complementary objective perspective to previously identified differences in means or amplitudes of suitable physiological variables, so that secretory typicality can be assessed quantitatively both on the basis of mean and amplitude level of output and on the basis of orderliness of the serial output. Strictly mathematically, there is a primary difference between regularity measures, such as ApEn, and moment statistics (e.g., means, standard deviations); viz, moment statistics, and their nonparametric counterparts are computed without regard to the order of the series to which they are applied. For ApEn, the order of the serial data is the crucial factor; discerning changes in order from apparently random to very regular is a primary focus of this statistic. Additionally, a direct statistical assessment of joint LH-testosterone network characteristics of either younger or aged men has not previously been accomplished, which cross-ApEn now addresses.

Clinically, a nontrivial implication of the present findings is the potential utility of both ApEn, and especially cross-ApEn, to separate the younger and older subject groups. This contrast may afford added physiological insight in instances when moment statistics and irregularity/asynchrony measures are not clinically redundant, even when hormone concentrations and ApEn lie within their respective normative ranges. The relative clarity of the young-old separation by ApEn and cross-ApEn takes on enhanced importance in light of reassessment of age-related changes in mean reproductive hormone levels, especially in the case of testosterone, for which there is no clear consensus. As deduced above, for nocturnal observations, mean serum testosterone concentrations are not necessarily distinguishable between very healthy young and older males. For immunoreactive LH, the inference of no overall mean level changes between young and older subjects has been verified by several studies, as well as by our above analysis.

More generally, quantification of signal regularity of both LH and testosterone release, as well as of their mutual relationship and synchrony, as illustrated here in relation to aging, could be employed to evaluate a variety of clinical disorders, and the efficacy of medical interventions. Furthermore, if a disorder is most prominently characterized by diminution of synchrony, methods to restore synchrony may require putatively novel therapeutic strategies. From an experimental perspective, studies are required to specify the source(s) determining synchrony, e.g. from the possibilities indicated above, and to perturb this source directly. However, even prior to this identification, one could attempt to restore synchrony obliquely, by providing dual, synchronous administration of agents that respectively induce LH and testosterone production. The point is that if a disorder is biologically determined by an overall system decoupling, a recoupling or reestablishment of temporal concordance may be required to restore physiological function, rather than any means of perturbing a single target node.

Mathematical and Statistical Properties of Cross-ApEn

To establish a theoretical statistical validity of cross-ApEn as employed above, a range of two-variable vector AR(2) processes were studied, and several types of coupled two-variable analogs of a "variable lag" process (described below) were studied. For each process, cross-ApEn(1, 0.2) was applied to standardized time-series (x-y pair) outputs, 50 replicates of N=150 point data lengths per process. For each process studied, the standard deviation (cross-ApEn) was less than or equal to 0.06, the standard deviation calculated from the cross-ApEn values from the 50 replicates; this imparts reasonable replicability properties similar to that known for ApEn. This degree of reproducibility is not unexpected, because qualitatively, cross-ApEn is a parameter that aggregates low-order, two variable joint distributions at a moderately coarse resolution (determined by r).

Mathematically, the need for ApEn, and particularly for cross-ApEn, is clarified by considering alternative parameters that might address similar concepts. In comparing two distinct signals or variables (e.g., to assess a degree of synchrony), primary parameters that one might employ include the cross-correlation function, and the cross-spectrum, with single variable counterparts the autocorrelation function and the power spectrum. Evaluation of these parameters often is insightful, but with relatively small length data sets, statistical estimation issues are nontrivial, and moreover, interpretation of the sample cross-correlation function is highly problematic, unless one employs a model-based prefiltering procedure. Furthermore, standard spectral estimation methods such as the fast Fourier transform (FFT) can be shown to be inconsistent or so badly biased that findings may be qualitatively incorrect, especially in the presence of outliers and nonstationarities. These difficulties are mirrored in the cross-spectrum, in addition to an often serious bias in estimation of coherency in short series.

Most importantly, the autocorrelation function and power spectrum, and their bivariate counterparts, are most illuminating in linear systems, e.g. seasonal autoregressive integrated moving average (SARIMA) models, for which a rich theoretical development exists. For many other classes of processes, these parameters often are much less effective at highlighting certain model characteristics, even apart from statistical considerations. To illustrate this point, consider the following simple model, denoted as a "variable lag" process, which includes a series of quiescent periods, of variable length duration, interspersed with identical positive pulses of a fixed amplitude and frequency. Formally, an integer time-valued process denoted VarLag is recursively defined having an $i^{th}$ epoch of a quiescent period of values equal to 0 at times $t_{i-1}+1, t_{i-1}+2, \ldots, t_{i-1}+lag_i$. This is immediately followed by the successive values sin ($\pi/6$), sin ($2\pi/6$), sin ($3\pi/6$), sin ($4\pi/6$), sin ($5\pi/6$), sin($6\pi/6$) equal to 0 at the next 6 time-units, where $lag_i$ is a random variable uniformly distributed on (i.e., randomly chosen between) the integers between 0 and 60, and $t_{i-1}$ denotes the last time-value of the $(i-1)^{st}$ sine-pulse.

Figure 18A:
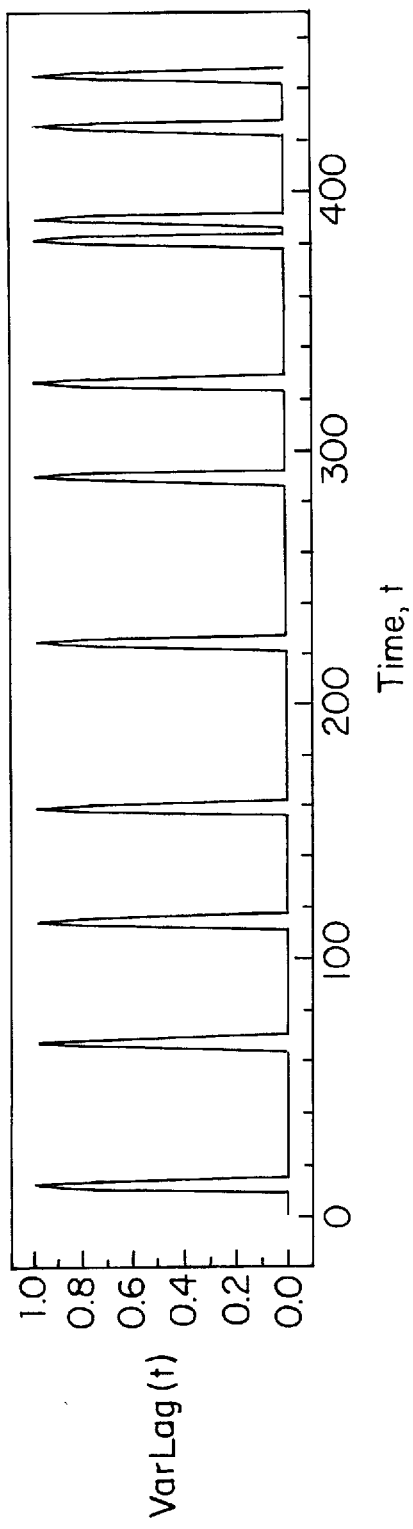
FIGS. 18A–18F are representative data output from a variable lag process in accordance with the invention.
Figure 18B:
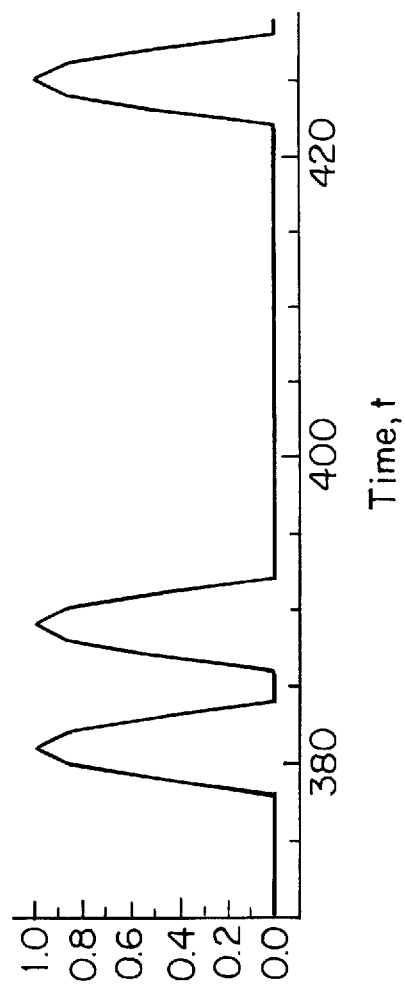
Figure 18C:
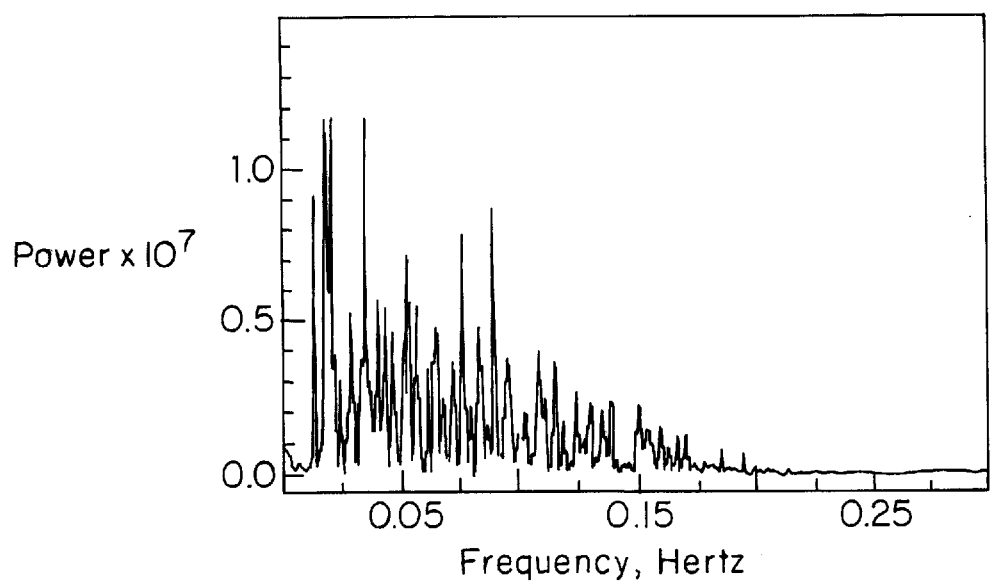
Figure 18D:
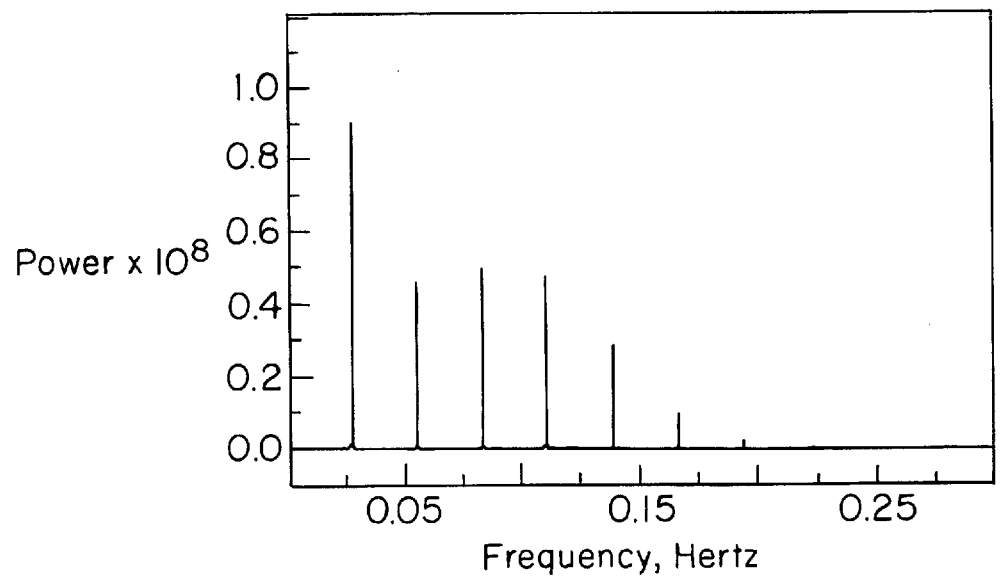
Figure 18E:
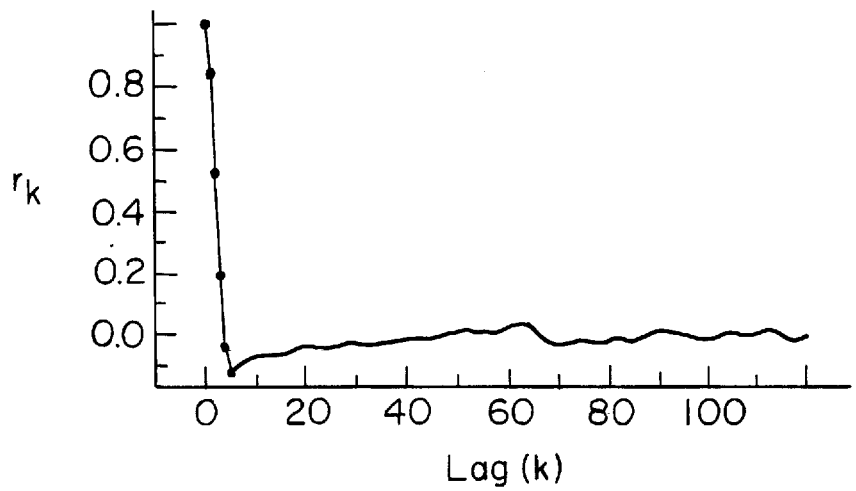
Figure 18F:
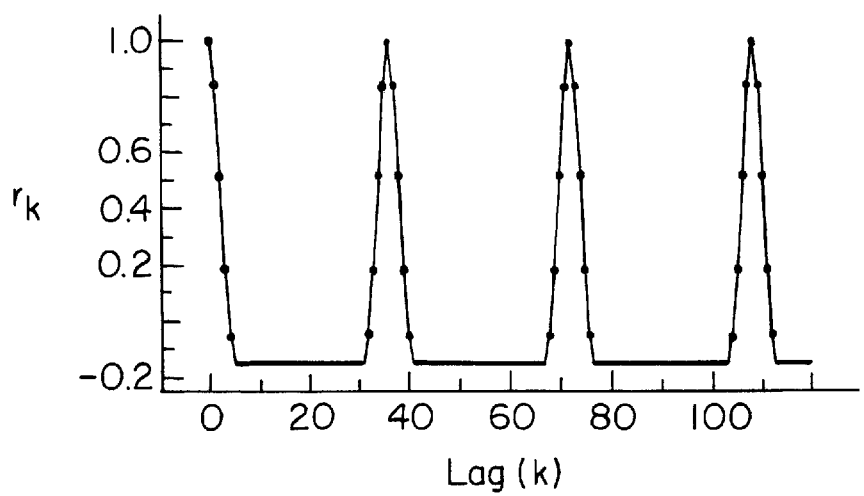

FIGS. 18A–18F are representative data output from VarLag demonstrating the utility of cross-ApEn. FIG. 18A is a representative output from this process, with FIG. 18B a closer view of this output near time t=400. FIG. 18C is the power spectrum for VarLag. FIG. 18D is the power spectrum for a constant (fixed) lag analog of VarLag. FIG. 18E is an autocorrelogram corresponding to FIG. 18C. FIG. 18F is an autocorrelogram corresponding to FIG. 18D. The power spectrum and autocorrelation function calculations shown in FIGS. 18C–18F were calculated from a realization of a time-series of length N=100,000 points.

Processes consisting of alternatingly quiescent and active periods would seem reasonable for biologists to consider, as they appear to model a wide variety of phenomena, especially in hormonal secretory dynamics. However, within mathematics, such processes with a variable quiescent period are not commonly studied. To the endocrinologist, output from the above model would be considered smoothly pulsatile, especially with the identical pulses; the variable lag process would be most readily distinguished from its constant lag counterpart (for which $lag_i$=30 time units for all i) via a decidedly positive standard deviation for the interpulse duration time-series, in the variable lag setting, as opposed to SD=0 (constant interpulse duration) in the constant lag setting. The essential point here, however, is that for VarLag, the power spectrum and autocorrelation function somewhat confound, as seen from FIGS. 18C and 18E. Based on these figures alone, the pulsatile nature of the time-series realizations is hardly evident, and for all $k \geq 6$, the autocorrelation coefficient $r_k$ at lag k is insignificantly different from 0. In contrast, the power spectrum and autocorrelation function confirm the periodicity of the constant lag analogue, shown in FIGS. 18D and 18F. Significantly, the issues here are in the parameters, rather than statistical inadequacies based on an insufficiently long output, or on artifacts (outliers), because FIGS. 18C–18F were derived from calculations based on 100,000 points from a purely theoretical model.

Similar limitations of the spectra and autocorrelation function are inherent to wide classes of processes. From a general mathematical framework, large classes of variable lag processes can be constructed simply by considering point processes, in which the "point" occurrence is replaced by a pulse occurrence, the pulse itself of either a fixed or variable form. The associated counting process could be of any character, and need not be so special as Poisson or renewal. Also, variable lags between events to be compared are the normative case in nonlinear (deterministic and stochastic) differential equations, in Poisson clumping models, and in output variables in typical (adaptive) control theory models and queueing network models. Notably, for many two-dimensional analogs of variable lag processes, and indeed for many two-dimensional systems in which no small set of dominant frequencies encapsulates most of the total power, the cross-spectrum and the cross-correlation function often will similarly fail to highlight episodicities in the underlying model and data, and thus fail to highlight concomitant changes to such episodic components.

In contrast to the autocorrelation function and spectral differences between the above variable lag and constant lag processes, the respective ApEn(1, 20% SD) values for the two processes are in close agreement: mean ApEn=0.195 for the variable lag process, while ApEn=0.199 for the constant lag setting (of course, ApEn for both these processes is much smaller than the clinically-derived values). This agreement in ApEn values manifests the primary requirement of matching (sub)patterns within data, while relaxing the requirement of a dominant set of frequencies at which these subpatterns occur. The two-variable analogue of ApEn, given by cross-ApEn, similarly enables one to assess synchrony in many classes of models. It thus should not be surprising that in the above study cross-correlation (Pearson-R) does not show significant group differences, whereas cross-ApEn does.

It should be emphasized, nonetheless, that FIGS. 18C–18F neither invalidate spectral power and (lagged) autocorrelation calculations, nor do they violate a properly oriented intuition. The broad-banded spectrum in FIG. 18C, and the negligible lagged autocorrelation in FIG. 18E for lag greater than or equal to six time-units, primarily reflect the independent, identically distributed, relatively broad distribution of the variable $lag_i$. Visually this conforms to viewing FIG. 18A from afar, in effect (nearly) ignoring the nature of each pulse, instead de facto primarily focusing on the "random" timing of the peaks as the process of interest. The viewpoint taken by ApEn is thus complementary to the spectrum and correlogram, more de facto focusing on (close-up) similarities between active pulses, e.g., from the perspective shown in FIG. 18B, while in effect nearly ignoring the nature of the quiescent epoch aspect of the process. The putative utility of ApEn and cross-ApEn to, for example, endocrinologists is based on the recognition that in many settings, changes in the episodic character of the active periods within pulsatile secretory time-series appear to mark physiologic and pathophysiologic changes—thus there is a concomitant need for quantitative methods that primarily address this perspective, e.g., ApEn and cross-ApEn.

In addition to the biological relevance of assessing LH and testosterone release from a distinct statistical perspective, the broad statistical utility of cross-ApEn is shown to quantify asynchrony or conditional irregularity in interconnected (e.g., hormonal) networks. This quantification strategy is relevant to many physiological feedback and control systems and to models for which cross-correlation and cross-spectral methods fail to fully highlight markedly changing features of the data sets under consideration.

Finally, cross-ApEn can be applied to a variety of paired variables in tightly or loosely interconnected systems. In multiple node networks, cross-ApEn can probe data pairwise to determine the weakest or altered paired links. For example, various hormone secretory time-series data can be paired, such as luteinizing hormone (LH), follicle-stimulating hormone (FSH), growth hormone (GH), insulin, glucose, testosterone, ACTH, cortisol, as well as other hormones. Also cardio-respiratory time-series data can be paired, such as electrocardiogram (ECG), heart rate derived from ECG, respiratory, blood pressure, and electroencephelogram (EEG). Also, there are multiple leads (time-series) recorded as an EEG. Thus cross-ApEn could be applied to any paired set of EEG lead data, potentially to localize site of abnormality, or type of disease (e.g., schizophrenia or diminution from partial head injury). Cross-ApEn can also be applied to various economic and finance time-series including market indices (e.g., Dow Jones, NASDAQ, bond markets, or paired among themselves or against external indicators, such as prime interest rate or political events).

Cross-ApEn can also be applied to aerodynamic, hydrodynamic, or flow variable time-series, which include pressure, velocity components (x, y, z coordinate directions), and speed. Depending on the particular application of cross-ApEn, the two sets of time-series data may not be collected during an overlapping time period and such use of temporally inconcurrent data sets is anticipated by the invention.

EQUIVALENTS

While the invention has been particularly shown and described with reference to preferred embodiments thereof, it will be understood by those skilled in the art that various changes in form and details may be made without departing from the spirit and scope of the invention as defined by the appended claims. In particular, the invention can be embodied in hardware, software or firmware.

These and all other equivalents are intended to be encompassed by the following claims.

The invention claimed is:

1. In a data processing environment, a method of processing a plurality of sets of data points to detect a system state, comprising the steps of:

with a processor, operating on a first set of data points and a second set of data points from a system, comprising the operating steps of:
 a) defining a first class of contiguous runs of a prescribed length for the first set of data points;
 b) defining a second class of contiguous runs of the prescribed length for the second set of data points;
 c) assigning quantitative values to measure the regularity and stability of similar patterns between the first and second sets of data points from the defined classes;
 d) aggregating the assigned quantitative values to quantify asynchrony between the first and second sets of data points; and determining a state of the system from the quantified asynchrony.

2. The method of claim 1 further comprising the step of providing at least one set of data points having values of a biological parameter measured from a living biosystem.

3. The method of claim 1 wherein the first and second sets of data points are time-series data, the first set of data points being temporally inconcurrent with the second set of data points.

4. The method of claim 1 wherein the step of aggregating comprises averaging the assigned quantitative values.

5. The method of claim 1 further comprising the step of providing at least one set of data points having values of a market indicator measured from a financial market.

6. The method of claim 1 further comprising at least one set of data points having values of a parameter measured from an electromechanical system.

7. The method of claim 6 wherein the electromechanical system is an aerodynamic system measuring gas flow parameters.

8. The method of claim 6 wherein the electromechanical system is a hydrodynamic system measuring fluid flow parameters.

9. The method of claim 1 wherein the processor operates on serial sets of data points.

10. In a data processing system, a method to detect a medical state from a plurality of biological signals from a living animal, comprising the steps of:

providing a first set of medical data points having values from a first biological signal;

providing a second set of medical data points having values from a second biological signal;

operating on the first and second sets of medical data points with a processor, comprising the operating steps of:
   a) defining a first class of contiguous runs of a prescribed length of the first set of medical data points;
   b) defining a second class of contiguous runs of the prescribed length of the second set of medical data points;
   c) assigning quantitative values to measure the regularity and stability of similar patterns between the first and second sets of medical data points from the defined classes;
   d) aggregating the assigned quantitative values to quantify asynchrony between the first and second biological signals; and determining a medical state of the living animal from the quantified asynchrony.

11. The method of claim 10 wherein at least one of the biological signals is a hormone secretion level.

12. The method of claim 10 wherein at least one of the biological signals is a cardio-respiratory time series.

13. The method of claim 10 wherein at least one of the biological signals is a respective electroencephelogram (EEG) time series.

14. The method of claim 10 wherein at least one of the biological signals is selected to detect a specific medical state.

15. The method of claim 14 wherein the specific medical state is female menopause.

16. The method of claim 14 wherein the specific medical state is a quantative hormonal change in a male.

17. The method of claim 10 wherein the first and second biological signals are selected to yield from the operating step a site of a medical condition in the animal body.

18. The method of claim 10 wherein the first and second sets of medical data points are time-series data, the first set of medical data points being temporally inconcurrent with the second set of medical data points.

19. The method of claim 10 wherein the step of aggregating comprises averaging the assigned quantitative values.

20. A computing apparatus for processing a plurality of sets of serial data points to detect a system state, the system comprising:
   a first set of data points having values from a first system signal of a system;
   a second set of data points having values from a second system signal of the system;
   a processor operating on the first and second sets of data points, the processor comprising the operating steps of:
      a) defining a first class of contiguous runs of a prescribed length of the first set of data points;
      b) defining a second class of contiguous runs of the prescribed length of the second set of data points;
      c) assigning quantitative values to measure the regularity and stability of similar patterns between the first and second sets of data points from the defined classes; and
      d) aggregating the assigned quantitative values to quantify asynchrony between the first and second sets of data points, the quantified asynchrony representing a state of the system.

21. The apparatus of claim 20 wherein at least one of the sets of data points comprises values of a biological parameter measured from a living being.

22. The apparatus of claim 20 wherein the first and second sets of data points are time-series data, the first set of data points being temporally inconcurrent with the second set of data points.

23. The apparatus of claim 20 wherein the step of aggregating comprises averaging the assigned quantitative values.

24. The apparatus of claim 20 wherein at least one of the sets of data points comprises values of a market indicator from a financial market.

25. The apparatus of claim 20 wherein at least one of the sets of data points compries values of a parameter measured from an electromechanical system.

26. The apparatus of claim 25 wherein the electromechanical system is an aerodynamic system and the measured parameters are gas flow parameters.

27. The apparatus of claim 25 wherein the electromechanical system is a hydrodynamic system measuring fluid flow parameters.

28. The apparatus of claim 20 wherein the processor operates on serial sets of data points.

29. A computing system to detect a medical state from a plurality of biological signals from a living animal, the system comprising:
   a first set of medical data points having values from a first biological signal;
   a second set of medical data points having values from a second biological signal;
   a processor operating on the first and second sets of medical data points, the processor comprising the operating steps of:
      a) defining a first class of contiguous runs of a prescribed length of the first set of medical data points;
      b) defining a second class of contiguous runs of the prescribed length of the second set of medical data points;
      c) assigning quantitative values to measure the regularity and stability of similar patterns between the first and second sets of medical data points from the defined classes; and
      d) aggregating the assigned quantitative values to quantify asynchrony between the first and second biological signals.

30. The system of claim 29 wherein at least one of the biological signals is a hormone secretion level.

31. The system of claim 29 wherein at least one of the biological signals is a cardio-respiratory time series.

32. The system of claim 29 wherein at least one of the biological signals is a respective electroencephelogram (EEG) time series.

33. The system of claim 29 wherein the first and second biological signals are selected to detect a specific medical state.

34. The system of claim 33 wherein the specific medical state is female menopause.

35. The system of claim 33 wherein the medical state is a quantitative hormonal change in a male.

36. The system of claim 29 wherein the first and second biological signals are selected to localize a site of a medical condition in the animal body.

37. The system of claim 29 wherein the first and second sets of medical data points are time-series data, the first set of medical data points being temporally inconcurrent with the second set of medical data points.

38. The system of claim 29 wherein the step of aggregating comprises averaging the assigned quantitative values.

* * * * *